United States Patent [19]

Swanson et al.

[11] Patent Number: 5,321,501
[45] Date of Patent: Jun. 14, 1994

[54] METHOD AND APPARATUS FOR OPTICAL IMAGING WITH MEANS FOR CONTROLLING THE LONGITUDINAL RANGE OF THE SAMPLE

[75] Inventors: Eric A. Swanson, Acton; David Huang; James G. Fujimoto, both of Cambridge; Carmen A. Puliafito, Weston; Charles P. Lin, Somerville; Joel S. Schuman, Wayland, all of Mass.

[73] Assignee: Massachusetts Institute of Technology, Cambridge, Mass.

[21] Appl. No.: 875,670

[22] Filed: Apr. 29, 1992

Related U.S. Application Data

[63] Continuation-in-part of Ser. No. 692,877, Apr. 29, 1991, abandoned.

[51] Int. Cl.$^5$ .............................................. G01B 9/02
[52] U.S. Cl. .................................. 356/345; 356/73.1; 356/346; 356/351; 250/227.27
[58] Field of Search .............. 356/345, 73.1, 346, 356/351; 250/227.27

[56] References Cited

U.S. PATENT DOCUMENTS 4,928,005  5/1990  Lefevre et al. .................. 250/227.23
5,202,745  4/1993  Sorin et al. ........................ 356/73.1

OTHER PUBLICATIONS

Youngquist & Davies, "Optical coherence-domain . . . technique", Optics Letters 12, 158–160, Mar. 1987.
Davies & Youngquist, "Method and apparatus . . . sites", UK Patent Application No. 8611055, May 7, 1987.
Takada, Yokohama, Chida & Noda, "New measurement system . . . technique", Applied Optics 26, 1603–1606, May 1, 1987.
Danielson & Whittenberg, "Guided-wave reflectometry w/micrometer resolution", Applied Optics 26, 2836–2842, Jul. 15, 1987.
Fercher, Mengedoht & Werner, "Eye-length measurement . . . light", Optic Letters 13, 186–188, Mar. 1988.
Beaud & Salthe, "Optical reflectometry w/micrometer . . . devices", IEEE Journal of Quantum Electronics 25, 755–759, Apr. 1989.
Gilgen & Beaud, "Submillimeter optical reflectometry", Journal of Lightwave Technology 7, 1225–1233, Aug. 1989.
Tateda & Horiguchi, "Water penetration sensing using . . . OTDR", IEEE Photonics Technology Letters 3, 1–3, Jan. 1991.
Hitzenberger, "Optical measurement of the axil . . . interferometry" Investigate Ophthal. & Visual Science 32, 616–624, Mar. 1991.
Kobayashi & Noda, "Polarization-independent . . .

(List continued on next page.)

Primary Examiner—Samuel A. Turner
Assistant Examiner—LaCharles Keesee
Attorney, Agent, or Firm—Wolf, Greenfield & Sacks

[57] ABSTRACT

A method and apparatus for performing optical imaging on a sample wherein longitudinal scanning or positioning in the sample is provided by either varying relative optical path lengths for an optical path leading to the sample and to a reference reflector, or by varying an optical characteristic of the output from an optical source applied to the apparatus. Transverse scanning in one or two dimensions is provided on the sample by providing controlled relative movement between the sample and a probe module in such direction and/or by steering optical radiation in the probe module to a selected transverse position. The probe module may be an external module or may be an endoscope or angioscope utilized for scanning internal channels. Multiple optical paths may be provided for parallel scanning and focus may be enhanced by varying the focal point in the sample in synchronism with longitudinal scanning of the sample.

46 Claims, 9 Drawing Sheets

OTHER PUBLICATIONS reflectometer", Journal of Lightwave Technology 9, 623–628, May 1991.

Kobayashi & Noda, "Optical fiber component . . . reflectometer", IEEE Photonics Technology Letters 3, 564–566, Jun. 1991.

Takada & Noda, "Reyleigh backscattering . . . spatial resolution", Applied Physics Letters 59, 143–145, Jul. 8, 1991.

Takada & Yukimatsu, "Resolution control of low . . . 14 and 290", IEEE Photonics Technology Letter 3, 676–678, Jul. 1991.

Huang & Fujimoto, "Micron-resolution ranging . . . reflectometry", Lasers in Surgery and Medicine 11, 419–425, 1991. (May, 1991).

Takada, Himeno & Yukimatsu, "Phase-noise . . . reflectometry", Applied Physics Letters 59, 2483–2486, Nov. 11, 1991.

Huang & Fujimoto, "Optical coherence tomography", Science 254, 1178–1181, Nov. 22, 1991.

Clivaz & Gilgen, "High-resolution reflectometry . . . tissues", Optics Letters 17, 4–6, Jan. 1, 1992.

Sorin & Gray, "Simultaneous thickness and . . . reflectometry", IEEE Photonics Technology Letters 4, 105–107, Jan. 1992.

Swanson & Puliafito, "High-speed optical . . . reflectometry", Optics Letters 17, 151–153, Jan. 15, 1992.

Hitzenberger & Fercher, "Measurement of corneal . . . inferometry", Investigative Opthal. & Visual Science 33, 98–103, Jan. 1992.

Kobayashi & Noda, "Polarization-independent . . . inferometry", Journal of Lightwave Technology 9, 0733-8724, May 1991.

METHOD AND APPARATUS FOR OPTICAL IMAGING WITH MEANS FOR CONTROLLING THE LONGITUDINAL RANGE OF THE SAMPLE

RELATED APPLICATIONS

This application is a continuation in part of application Ser. No. 07/692,877, filed Apr. 29, 1991, now abandoned, the contents of which is incorporated herein by reference.

FIELD OF THE INVENTION

This invention related to optical imaging, including utilizing such images to perform precision measurements on biological and other samples.

BACKGROUND OF THE INVENTION

There are may industrial, medical, and other applications where high resolution (generally less than 10 micrometer) images of, and measurements of distances, thicknesses, and optical properties of, a biological or other sample are required.

Copending application Ser. No. 07/692,877 mentioned above describes an optical coherence domain reflectometer (OCDR) technique for performing such measurements generally with a single scan in the longitudinal direction. However, there are many applications, including medical applications, where a need exists for such scans to be conducted in two or three dimensions rather than in a single dimension, including transverse directions at a given longitudinal depth, thereby providing multidimensional imaging and measurements. Therefore, a need exists for a means to perform such scanning in at least one transverse direction at a selected longitudinal depth, with the capability of also scanning in the longitudinal direction.

Further, particularly in medical application, it is frequently desirable to provide such scans inside of tubular or other structures such as blood vessels, the bronchial tree of the lungs, the gastrointestinal tract, the genital tract or the urinary tract, using an angioscope or endoscope. In order for such scanning to be performed, a probe must be provided which is capable of being mounted in an endoscope or angioscope for performing internal scans.

While typically a scan would be completed through the full depth range at a given lateral and/or transverse position before repositioning to the next position, this may require scanning of the mirror or other element used for performing longitudinal range or depth scans at a rate higher than the capacity of existing equipment. This is particularly true where the longitudinal scan produces a Doppler shift frequency which affects the interferometric signal frequency and hence the system sensitivity. It is, therefore, desired that such scanning be performed at a constant velocity. However, since very high speed longitudinal scanning at a constant velocity is difficult to achieve, where two or three dimensional scanning is being performed, other scan patterns may be required. Further, in some applications, it may be desirable to perform transverse scanning in one or two dimensions at a selected longitudinal position or depth.

Another problem which becomes particularly serious when transverse scanning is being performed is that the bandwidth of the received signals increases beyond the inherent Doppler frequency shift of the system. In such cases, aliasing (i.e. variations in image intensity) may occur. It is, therefore, desirable that a technique be provided to enhance resolution by eliminating or averaging out such intensity variations.

Another problem with the prior system is that, if scanning is to be conducted over an extended depth range, a smaller numerical aperture must be used so as to extend the depth of focus. However, this reduces lateral resolution and the received optical signal power throughout the range. A need, therefore, exists for a technique which permits the use of a large numerical aperture over an extended depth range within a sample.

Further, some of the problems described which result from performing longitudinal scanning by mechanically moving a mirror or other element may be overcome by performing this scan electronically, for example by varying the optical frequency or amplitude of the light incident from the light source. However, for certain applications, for example imaging a dynamic biological sample such as the eye, the scanning speed required to do three-dimensional scanning may be such that a parallel scanning technique may be preferable or may be required.

SUMMARY OF THE INVENTION

Thus, a need exists for improved optical coherence domain reflectometer (OCDR) optical imaging and measurement systems or for other imaging and measurement systems, particularly electronically scanned systems, which are capable of performing two and three dimensional scans at a selected and/or over an extended longitudinal or depth range for either internal or external samples with sharp focus and high resolution and sensitivity over the range.

In accordance with the above, this invention provides a method and apparatus for performing optical imaging on a sample by applying optical radiation, which radiation has a short coherence length for preferred embodiments, to a reference optical reflector and to the sample through first and second optical paths respectively. The optical paths are preferably fiber optic paths. The longitudinal range within the sample from which imaging information is obtained is controlled by, for example, altering the relative lengths of the paths or by varying the frequency or intensity of the source in accordance with a predetermined profile. The lateral or transverse position on the sample at which imaging or measurements are being performed is also selectively changed. This results in imaging being performed on the sample in at least one transverse dimension. Where the profile for longitudinal scanning is a steppable profile, transverse scanning in one or two dimensions may be performed at any selected longitudinal range. Reflections from the reflector through the first optical path and reflections from the sample received through the second optical path are combined, the resulting combined optical output having interference fringed at matched points, for example, length matched points, on the two paths and having an instantaneous modulating frequency which may include a Doppler shift frequency at a frequency $f_D \sim NV/\lambda$ for embodiments where relative path lengths are being altered with a velocity profile having an instantaneous velocity V at each point on the profile. The combined output is detected and the detected output is processed to obtain a selected image of the sample.

The second optical path is preferably terminated in a probe module which includes a means for controlling the transverse position on the sample at which imaging is being performed, and a means for selectively changing this position in at least one dimension to scan the sample. The velocity V may be sufficiently high so that the Doppler shift frequency is sufficiently high to meet the bandwidth requirements to overcome the predominate low frequency noise for the system and for signal aliasing. Where this is not the case, a means is provided for causing a vibratory or other change in a modulating frequency $f_M$, resulting in a modulating frequency which is a selected combination of $f_D$ and $f_M$. This change may be effected by at least one acousto-optic modulator (AOM) in at least one of the optical paths. For one embodiment, there are two AOM's in one of the optical paths, with $f_M$ being the difference frequency shift caused by the two AOM's. The probe position controller may include means for moving a probe at the end of the second optical path or the distal end of a fiber optic element forming the second optical path in at least one dimension substantially perpendicular to the direction in which optical radiation is applied to the sample to provide two-dimensional or three-dimensional scanning of the sample.

For other embodiments, the probe module may include mirrors or other means for steering the optical radiation to a position on the sample and for optically changing the transverse position in at least one dimension, generally perpendicular to the direction in which the optical radiation is applied to the sample. Where three dimensional scanning is desired, the transverse position is changed in two directions. The means for optically changing transverse position may include at least one movable mirror in the optical path of the radiation for angularly translating the radiation at an angle dependent on mirror position. One mirror may be movable in two orthogonal directions to angularly translate the radiation in a direction which varies in two dimensions, whereby three dimensional scanning is achieved, or this objective may be achieved utilizing two mirrors successively spaced along the optical path, with the mirrors being movable in different, generally orthogonal, directions.

For other embodiments, the probe module is a mechanism for scanning internal channels such as an angioscope or endoscope. For such applications, the probe module may include an outer sheath. For one embodiment, the probe module also includes an inner sheath rotatably mounted within the outer sheath, an optical means for directing radiation from the second optical path through the inner sheath, and a means movable with the inner sheath for directing the radiation at a selected position on the internal channel, the selected position varying as the inner sheath is rotated. This embodiment preferably uses a mirror mounted to rotate with the inner sheath to reflect radiation passing through the inner sheath in a selected direction beyond the end of the outer sheath.

For another embodiment, a bundle of optical fibers is mounted in the outer sheath. A first end of a selected one or more of such optical fibers are optically connected to the second optical path, a means being provided for controlling the optical fiber(s) to which the second optical path is connected. There is also a means for establishing a selected transverse position on the sample for each of the optical fibers and for optically connecting a second end of each optical fiber to the corresponding selected transverse position.

For still another embodiment, wherein the first and second optical paths are in the form of first and second optical fibers respectively, the probe includes a means for securing a distal end of the second optical fiber to an inner wall of the sheath. This means includes means for moving the distal end toward and away from the wall. Means are also provided for optically connecting the distal end of the fiber to the sample, this means establishing a selected focal position on the sample for each position of the distal end relative to the wall.

For some embodiments, the probe module includes a means for controlling the focus for the module in the sample so that this depth focus is maintained substantially at a point in the sample from which imaging information is being obtained as this point is periodically changed during a longitudinal scan of the sample. Such focal plane may be accomplished by moving a focusing lens of the probe module in the direction of the radiation passing therethrough to control focus depth.

Multi-dimensional scanning may be accomplished utilizing at least three different scan patterns. For one scan pattern, the rates at which the relative lengths of the optical paths are altered and at which the transverse position on the sample is changed are such that points at all longitudinal ranges of interest are scanned for a given sample transverse position before the scan beam is moved to initiate imaging at a new transverse position. Alternatively, the relative rates at which the longitudinal range altering and sample transverse position changing occur may be such that all imaging positions in at least one transverse dimension are scanned at a given longitudinal range in the sample before the longitudinal range is altered to cause scanning at a new range to be performed. The latter scanning procedure may be desirable where very high speed, uniform velocity longitudinal scanning would be required if the first scanning pattern were utilized. A third scanning pattern is to step the longitudinal position control to a selected longitudinal position and to then perform scanning in one or two dimensions ar such longitudinal positions.

For some embodiments, a plurality of optical paths may be provided to permit parallel scanning on the sample. In addition, for some embodiments a characteristic of the optical source, such as its frequency or intensity is controlled or varied to control the longitudinal point in the sample being imaged, the received reflections resulting in an output having a frequency proportional to the optical length of the path to the longitudinal point or plane in the sample being imaged at the time. This output is detected and processed to obtain the image.

Because of aliasing or other problems, spurious intensity variations may occur in an image produced as a result of a two or three dimensional scan. To overcome this problem, AOM's may be used as previously indicated or a plurality of scans may be performed on a sample, with the scans being averaged to compensate for intensity variations.

For preferred embodiments, the measurements involve non-invasive cross-sectional imaging in biological specimens. One particular useful application for the invention is in producing cross-sectional images of various eye sections.

The foregoing and other objects, features and advantages of the invention will be apparent from the following more particular description of preferred embodiments of the invention as illustrated in the accompanying drawings.

IN THE DRAWINGS

DETAILED DESCRIPTION

Figure 1A:
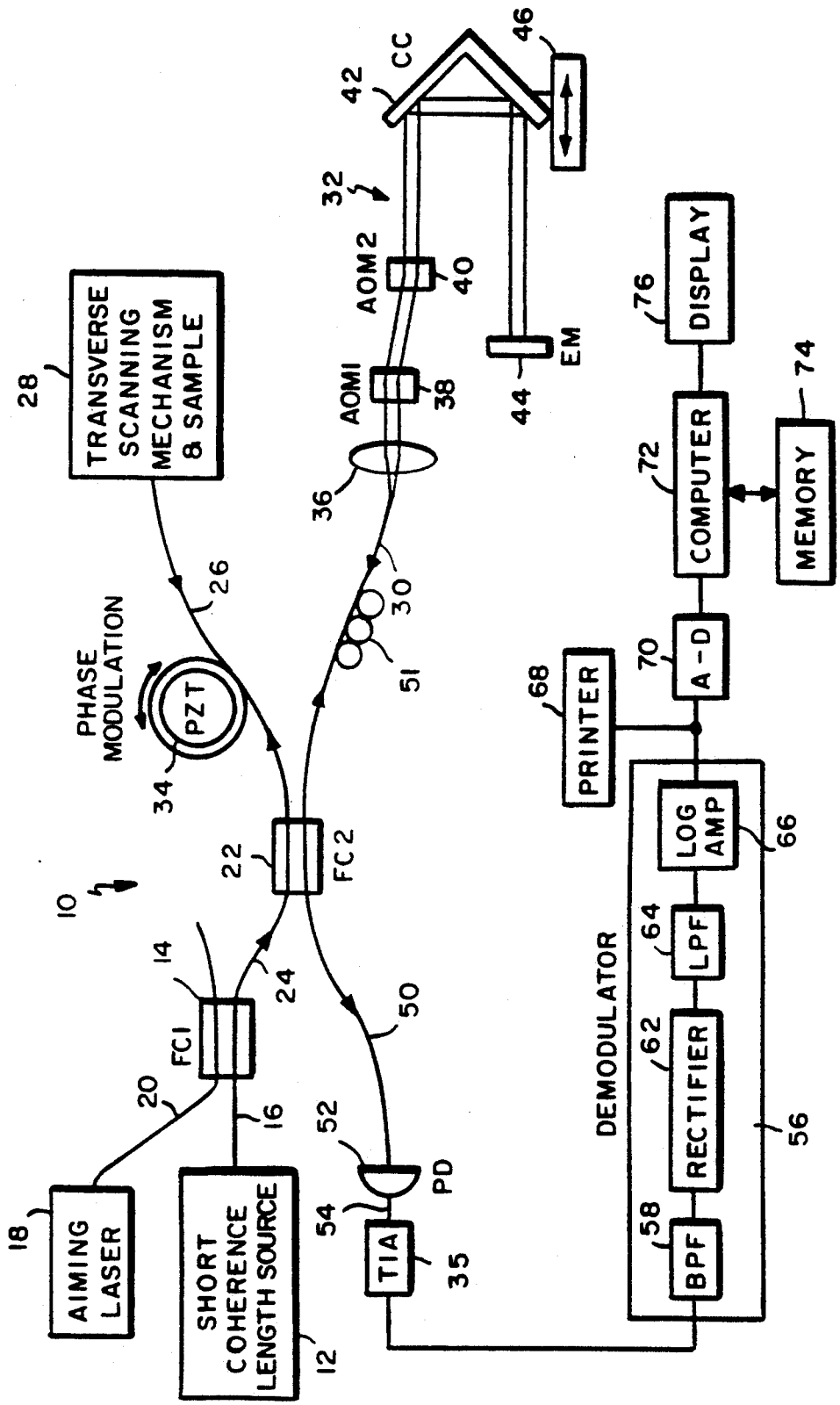
FIG. 1A is a schematic block diagram of an optical coherence domain reflectometer in accordance with a preferred embodiment of the invention.

Referring first to FIG. 1A, an optical coherence domain reflectometer (OCDR) 10 is shown which incorporates the teachings of this invention. In particular, the output from a short coherence length (broad spectral bandwidth) optical source 12 is coupled as one input to an optical coupler 14. Such coupling may be through a suitable optical path, which for the preferred embodiment is a fiber optic path 16. Source 12 may, for example, be a light emitting diode, super luminescent diode or other white light source of suitable wavelength, or may be a short-pulse laser. Such sources preferably having a coherence length of less than 10 micrometers for preferred embodiments. As will be discussed later, it is desirable that the coherence length of source 12 be minimized to enhance the resolution of the system.

The other input to coupler 14 is from a laser 18 generating an optically visible output which is applied to the coupler through a fiber optic path 20. As is discussed in greater detail in the copending application, laser 18 does not contribute to the normal operation of the system and is utilized only to provide a source of visible light for proper alignment with a sample, when the light from diode 12 is in the infrared region and thus not visible.

The output from coupler 14 is applied as an input to coupler 22 through fiber optic path 24. The light or optical energy received at coupler 22 is split between a first fiber optic path 26 leading to scanning/sample assembly 28 and a second fiber optic path 30 leading to a reference assembly 32. Assembly 28 may include a lens assembly formed of one or more lenses for focusing light received from optical path 26 on a sample to be scanned and various mechanisms for causing lateral, transverse or longitudinal motion of the light relative to the sample. In particular, while for the preferred embodiment longitudinal scanning is performed by movement at the reference assembly, it is also possible for the sample or probe to be moved longitudinally, or for longitudinal scanning to otherwise be performed at assembly 28. The assembly may also include a mechanism for controlling the longitudinal or depth position of the focus in conjunction with the longitudinal scan position. A probe module portion of assembly 28 may be designed for positioning adjacent to an outer surface of the sample, for example adjacent to a patient's eye for scanning and imaging or taking measurements on the patient's eye, or it may be adapted to be positioned inside the sample, being, for example, part of an angioscope or endoscope for scanning internal body or other channels. For purposes of FIG. 1A, the sample being scanned and/or imaged is included in the assembly 28. Various mechanisms which may function as the assembly 28 in accordance with various embodiments of the invention are shown in FIGS. 2-7.

For all embodiments, light transmitted by the probe to the sample is reflected by the sample back through the probe module to fiber 26. The optical fiber of path 26 may be wrapped around a piezoelectric crystal transducer or actuator 34 which vibrates (i.e. expands and contracts) in response to an applied electrical signal to cause slight expansion and contraction of the optical fiber and to thus modulate the optical signal passing through the fiber. As will be discussed later, this added modulation may facilitate detection.

Reference assembly 32 may include a collimating lens 36, first and second acousto-optic modulators 38 and 40 (AOM 1 and AOM 2), a corner-cube retro-reflector 42 and an end mirror 44. For the preferred embodiment, corner cube 46 is mounted to a mechanism 46 which reciprocates the corner cube toward and away from both optical path 30 and end mirror 44 in a particular pattern to effect longitudinal scanning of the sample. As discussed in greater detail in the beforementioned copending application, the corner-cube is preferably moved at a uniform, relatively high velocity (for example greater than 1 CM/SEC), causing Doppler shift modulation used to perform heterodyne detection. The length or extent of movement of cube 42 by mechanism 46 is at least slightly greater than half the desired scanned depth range in the sample. The scanning pattern for mechanism 46 preferably has a uniform velocity V, at least during the portions thereof during which scanning occurs, and may, for example, be a ramp pattern, or a sawtooth pattern. Further, as discussed in the copending application, a sine wave or other scan pattern can be utilized with suitable compensation in other elements of the circuit.

Alternatively, scanning in the longitudinal or depth dimension may be accomplished by reciprocating end mirror 44 with a suitable mechanism such as mechanism 46 rather than corner cube 42. However, if this is done, the effective stroke is reduced by 50% so that the end mirror 44 must be moved through a path which is slightly greater than the desired scan depth range rather than through a path equal to half such range. The greater travel stroke required for the mechanism 44 in this instance may adversely affect the scan rate achievable and may also limit the modulating Doppler shift frequency, requiring the use of additional modulating elements. If corner cube 46 is eliminated completely, the system becomes more susceptible to errors resulting from wobble of the end mirror as it is reciprocated.

It is also possible to eliminate the end mirror by arranging the corner cube for a single pass configuration. In this configuration, incoming light to the corner cube is aligned with the corner cube vertex. This also results in a 50% decrease in the effective stroke. In addition, as discussed above, mechanism 46 may be eliminated in the reference assembly 32, with longitudinal scanning being performed in assembly 28 by moving either the probe or sample in the longitudinal direction. This will be discussed later. If this is done, then corner cube 42 is not required and light from path 30 may impinge directly on mirror 44.

Finally, while for preferred embodiments utilizing a Doppler shift frequency, mechanism 46 moves a corner cube or end mirror at a velocity which, as indicated above, is substantially constant in the scanning range, for some embodiments to be discussed, Doppler shift modulation in the longitudinal direction is not utilized and movement of the mirror is effected primarily to control the desired scan depth. For such embodiments and others, mechanism 46 may operate in step fashion to control the desired scan depth.

The total length of path 26 between coupler 22 and a selected depth point in a sample being scanned and the total length of path 30 between coupler 22 and end mirror 44, should be substantially equal for each depth point of the sample during a scan of selected depth range. In addition, to prevent group velocity dispersion which would decrease spatial resolution, the lengths of the optical fibers in paths 26 and 30 should also be substantially equal. Alternatively, the group velocity dispersion may be equalized by placing optical materials of known group velocity dispersion and thickness in the light paths to compensate for any inequality. For example, where the fiber in the reference path may need to be shorter than that in the sample probe, a length of high dispersion material may be included in the reference path. It is also important that the termination of the optical fibers utilized in this system be angle polished and/or anti-reflection coated to minimize reflections and maximize throughput.

Mechanism 46 may be any one of a variety of devices adapted for performing the translation function. For example, mechanism 46 could be a stepper motor, the motion of which is applied to corner-cube 42 or mirror 44 through an averaging mechanism for embodiments where uniform velocity is required. A DC servo-motor might also be utilized to obtain the desired motion. Various electromagnetic actuators, for example a speaker coil, may also be utilized for this function. With such electromagnetic actuators, detection of mirror position and servo control thereof may be required in order to achieve uniform motion where required. More specifically, in a uniform motion system, a signal indicative of desired mirror position at each point in the mirror travel path could be compared against a signal from a detector of actual mirror position and any resulting error signals utilized to control the actuator to maintain the mirror moving at the desired constant velocity. It is also possible to use a servo control galvanometer driven linear translator for the mechanism 46.

One potential problem in the reference mechanism 32 is wobble of the mirror being translated which may adversely effect the accuracy of distance determinations. Such wobble is partially compensated for in the embodiment of FIG. 1A by corner-cube 42, such corner cubes generally having the property that, regardless of the angle at which a beam is incident thereon, the beam will always return in exactly the same direction at which the beam was incident. Other techniques known in the art and/or discussed in the before-mentioned copending application may also be utilized to deal with the wobble problem.

Reflections received from assemblies 28 and 32 are applied through optical paths 26 and 30, respectively to optical coupler 22. These signals are combined in coupler 22, resulting in interference fringes for length-matched reflections, (i.e. reflections for which the difference in reflection path length is less than the source coherence length) and the resulting combined output is coupled onto fiber optic path 50.

To maximize interference between light returning from the reference and sample optical paths, their polarization should be substantially the same. To accomplish this polarization matching, a polarization controller may be placed in one of the optical paths 26 or 30. For purposes of illustration, a polarization controller 51 is shown in optical path 30 in FIG. 1A. Such a polarization controller compensates for changes in polarization in the fiber optic paths. Alternatively, polarization maintaining fibers and couplers may be utilized in the system to achieve the desired result. Further, in applications where polarization is randomly varying, a polarization diversity receiver can be utilized in the system to eliminate signal fading. Such polarization diversity receivers are known in the art.

The optical signal on fiber optic path 50 is applied to a photodetector 52 which converts the optical combined signal from path 50 to a corresponding current-varying electrical signal. The current-varying electrical signal on output line 54 from photodetector 52 is preferably converted to a voltage-varying signal by a transimpedance amplifier (TIA) 55 or other suitable means, the TIA output being applied as an input to a demodulator 56.

Various forms of demodulation may be utilized in practicing the teachings or this invention. In its simplest form, demodulator 56 may consist of a bandpass filter 58 centered around the modulation frequency of the combined output signal and an envelope detector. The filter assures that only the signal of interest is looked at and removes noise from the output. This enhances the signal-to-noise ratio of the system and thus system sensitivity. The filtered signal is then applied to the envelope detector.

The envelope detector in demodulator 46 may consist of a rectifier 62 and a subsequent low pass filter 64. The second filter removes any high frequency components from the base band signal. The demodulator may also include a logrithmic amplifier 66, either before or after the rectifier, for dynamic range compression. Where a logarithmic amplifier is not used, logarithmic compression may be performed elsewhere in the system, for example in the processing computer. Without logarithmic compression, strong reflections from boundaries would either be off scale or weaker reflections would not be visible.

The exemplary demodulator described above is one type of heterodyne demodulator. However, a variety of other demodulation techniques known in the art may also be utilized to perform the demodulator function.

The demodulated output from circuit 56 is the interferometric envelope signal of interest. A suitable printer 68 may be utilized to obtain a visual record of this analog signal which may be utilized by a doctor, engineer or other person for various purposes. For preferred embodiments, the analog output from demodulator 56 is applied, either in addition to or instead of to printer 68, through an analog-to-digital converter 72 to a suitable computer 74 which is programmed to perform desired analysis thereon. One or more memory devices 74 may be provided with computer 72. Computer 72 may, for example, control the display of the demodulated signal on a suitable display device 76, such as a cathode ray tube monitor, or may control a suitable printer to generate a desired record.

Where a printer or a computer display is utilized to reproduce the scanned image, characteristics such as density of the scanned image may be reproduced utilizing gray scale levels (i.e. dark for high density and light for low density) or a "false color" image may be generated with the color from blue to red across the color spectrum being indicative of the characteristic. In addition, computer 72 may detect various points of interest in the demodulated envelope signal and may perform measurements or make other useful determinations based on such detections. Computer 72 may be a suitably programmed standard processor or a special purpose processor may be provided for performing some or all of the required functions.

The OCDR shown in FIG. 1A may for some embodiment be utilized with corner cube 42 being scanned by mechanism 46 at an intermediate but uniform velocity. For purposes of this discussion, an intermediate scanning velocity is considered one at which the Doppler frequency shift caused by cube or mirror movement is not negligible, but is low enough to fall within the predominant low frequency noise for the system. The noise spectrum includes noises arising from fluctuations in source 12, mechanical components and electrical circuits, and are larger at lower frequencies, typically below 10 kHz. High scan velocity is considered to be a velocity where the Doppler frequency shift is higher than the predominant low frequency noise. The Doppler shift frequency $f_D$ results from the translation of the cube 42 and, with a corner-cube, is given by the equation: $f_D \sim 4 V/\lambda$ where V is the velocity at which the cube is being moved at the given time and $\lambda$ is the optical wavelength of the source. Where a corner-cube is not used, $f_D \sim 2 V/\lambda$. Thus, in addition to compensating for wobble as the mirror is translated, the corner-cube also doubles the Doppler shift frequency, and effective scanning stroke, for a given velocity V of the mechanism 46.

Where this Doppler shift is less than the required bandwidth to overcome noise, including where stepped longitudinal or no longitudinal scanning is being performed so that the Doppler shift frequency is substantially zero, additional modulation is needed to shift the modulation frequency above the predominant noise spectrum. In FIG. 1A, this may be achieved by introducing sinusoidal phase modulation by use of piezoelectric transducer 34. While in FIG. 1A the additional modulation is introduced by use of the oscillator or transducer in sample path 26, such modulation could also be provided in the reference arm or path 30. Equivalent piezoelectric modulation of end mirror 44 could also be utilized. Further, in addition to piezoelectric transducer 34, the small movement required for this supplemental modulation may be achieved using electromagnetic, electrostatic, or other elements known in the art for providing small generally sine wave movements.

Alternatively, as shown in FIG. 1A, this supplemental modulation can be achieved by passing light in the reference arm and/or sample arm through acousto-optic modulators (AOM's). Such modulators produce a frequency shift of the light beam and thus produce an effect substantially equivalent to Doppler shifting the beam. Such acousto-optic modulators can, in some instances, be substituted for the movement of the mirror or corner cube. The AOM's, which can be bulk optical devices as shown in FIG. 1A or, may be smaller in-line optical fiber AOM's, effectively raise the carrier frequency to allow for high speed scanning. While one AOM may be adequate for this purpose, two AOM's can be used as shown in FIG. 1A. The reason for two AOM's is that since AOM's are normally driven at a much higher frequency then is required for this application, the detection frequency can be lowered to a desired frequency by driving two AOM's at different frequencies, the detector frequency being the difference frequency.

Supplemental modulation from element 34, or from other suitable means which modulate the optical path length, is at a frequency $f_M$ and the oscillation amplitude of this modulator is adjusted so that the peak-to-peak oscillating movement or optical delay change is approximately one-half of the wavelength $\lambda$ of source 12. The combined effect of the supplemental modulation and the Doppler shift frequency causes the output envelope to be at modulating frequencies of $f_D$, $f_M+f_D$, $f_M-f_D$ and at higher harmonics of $f_M \pm f_D$. $f_M$ is normally chosen to be high enough to overcome noise spectrum and aliasing problems.

Demodulation of the output from photodetector 54 is normally at $f_M+f_D$ and/or $f_M-f_D$. For purposes of illustration, it will be assumed that demodulation is at $f_M+f_D$. The center frequency for bandpass filter 58 is thus set for the frequency ($f_M+f_D$). The bandwidth for filter 58 should be approximately two to three times the full-width-half-maximum (FWHM) bandwidth or the received signal to avoid signal broadening and distortion. The bandwidth of low pass filter 64 would typically be roughly identical to that of bandpass filter 58. While if the velocity at which cube 42 is being moved has a high enough speed so that the resulting Doppler shift frequency is higher than the predominant noise spectrum and wide enough so that transverse scanning does not cause signal aliasing, then supplemental modulation by devices such as modulators 34, 38, 40 is not required, this may not be possible with two-dimensional or three-dimensional scanning because of the broad bandwidth involved.

For the embodiments discussed to this point, the scanning of cube 42 has been at constant velocity, at least through the scan interval. However, for very high speed scanning ar high scan repetition rates that cannot be realized with servo-controlled constant velocity mechanical drives, resonantly (sinusoidal) driven mechanical actuators can be used to drive cube 42 or mirror 44. These actuators can be galvanometrically or electrodynamically driven at the resonant frequencies of the mechanical actuator system and are commercially available. Adjustments to the system required to accommodate a sinusoidal drive are discussed in the beforementioned copending application. Alternatively, where higher speed scanning is required, electro-optic techniques could be used in lieu of mechanical techniques to effect scanning. For example, an acousto optic modulator or other electro-optic modulator could be utilized to vary the light path. However, such devices are currently expensive and have limited range; such devices would therefore not be preferred for most applications.

Figure 1B:
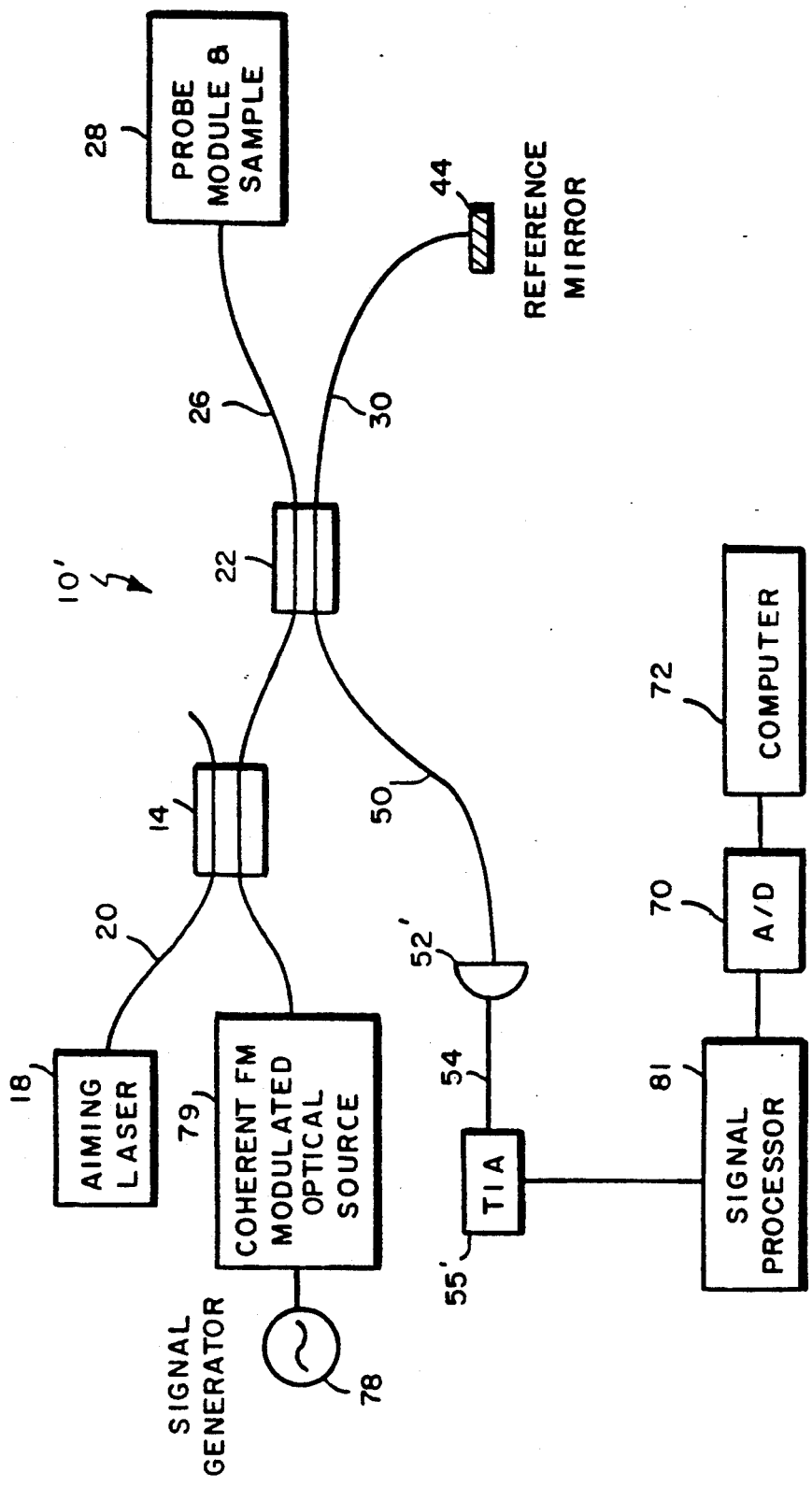
FIG. 1B is a schematic block diagram of an alternative embodiment of the invention utilizing a frequency modulated optical source.

FIG. 1B illustrates an alternate embodiment of the invention wherein longitudinal ranging information is obtained by optical frequency domain reflectometry rather than by optical coherence domain reflectometry. In this figure, and in the remaining figures, the same reference numerals are utilized to identify common elements. A prime number may be utilized to identify a common element with a prior figure where the element has been slightly modified.

FIG. 1B shows an optical frequency domain reflectometer utilizing a spectrally coherent optical source 79 which is frequency modulatable in one of a number of ways known in the art. Source 79 is frequency modulated in the form of a linear FM chirp by signal generator 78. The output from source 79 passes through the same optical paths described in conjunction with FIG. 1A to a sample assembly 28 and to a reference mirror 44. Since changes in optical path length are not being utilized for this embodiment of the invention to perform longitudinal scanning, the remainder of the reference assembly shown in FIG. 1A is not required nor are modulators 34, 38 and 40. A lens such as lens 36 may or may not be required.

Reflected radiation from the sample in assembly 28 and from reference mirror 44 are combined in fiber optic coupler 22 and directed through optical path 50 to a wide bandwidth photodetector 52' where they optically interfere. Wide bandwidth photodetector 52' and transimpedance amplifier 55' are used to amplify the detected signal. The detected optical interference generates an RF frequency that is proportional to the differential path length between the sample reflection and the reflection from reference mirror 44. A variety of methods known in the art exist to convert this frequency information into spatial information in an electrical processor 81. These include using a waveform recorder with inverse Fourier transform techniques. Requirements on and techniques to achieve linearity, spectra coherence, modulation bandwidth and frequency deviation are all known in the art and such techniques can be employed in the embodiment of FIG. 1B. The output from processor 81 is digitized using A/D converter 70 and processed by computer 72 in the manner discussed in conjunction with FIG. 1A. Printers and displays may be provided for this embodiment of the invention as for the embodiment shown in FIG. 1A. With suitable modifications, the teachings of the invention may also be practiced employing a linearly chirped intensity modulated source.

Figure 2:
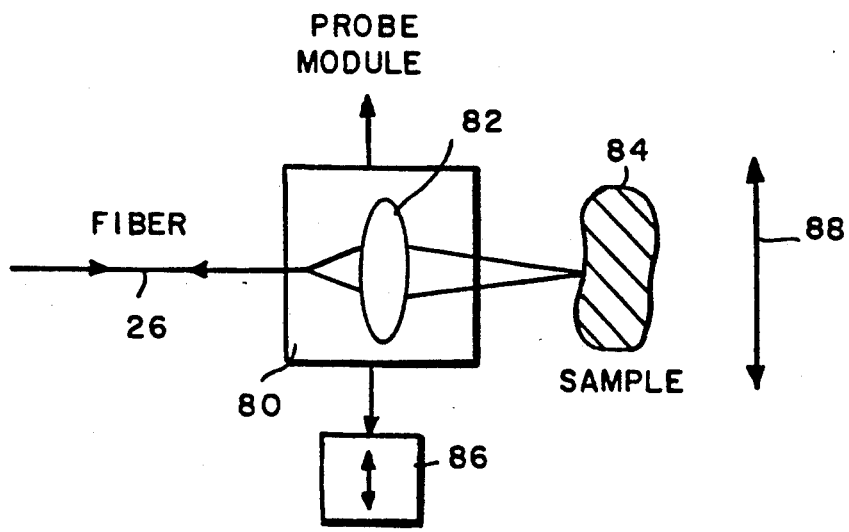
FIG. 2 is a block diagram illustrating One embodiment of a probe module to achieve multi-dimensional scanning.

FIG. 2 illustrates one relatively simple embodiment for the assembly 28 of FIGS. 1A–1C. For this embodiment, fiber 26 terminates in a probe module 80. The probe module includes one or more imaging lenses, a single lens 82 being shown in the figure, positioned between the output of fiber 26 and the sample 84 being scanned. A suitable linear translation stage or other mechanism 86 is connected to move probe module 80 either transversely or laterally relative to the sample 84 to provide two-dimensional scanning. A similar mechanism (not shown) may be provided to move the probe in the other of the transverse or lateral direction to provide three-dimensional scanning of sample 84. (Transverse and lateral scanning are sometimes collectively referred to hereinafter as transverse scanning.) Mechanism 86 may be a stepper motor or other suitable positioning mechanism and is preferably controlled either by computer 72 (FIG. 1) or by a positioning computer which also provides positioning information to computer 72 so that the position of the scan on sample 84 is known by the computer. Alternatively, probe module 80 may remain stationary and sample 84 can be translated in one or two dimensions, as illustrated by arrow 88, to effect the desired multi-dimensional scanning. Further, as previously discussed, either probe module 80 or sample 84 may be moved in the longitudinal direction by a suitable translating mechanism to effect longitudinal position for scanning. This would be done in lieu of or in conjunction with moving the corner cube or end mirror.

Figure 3A:
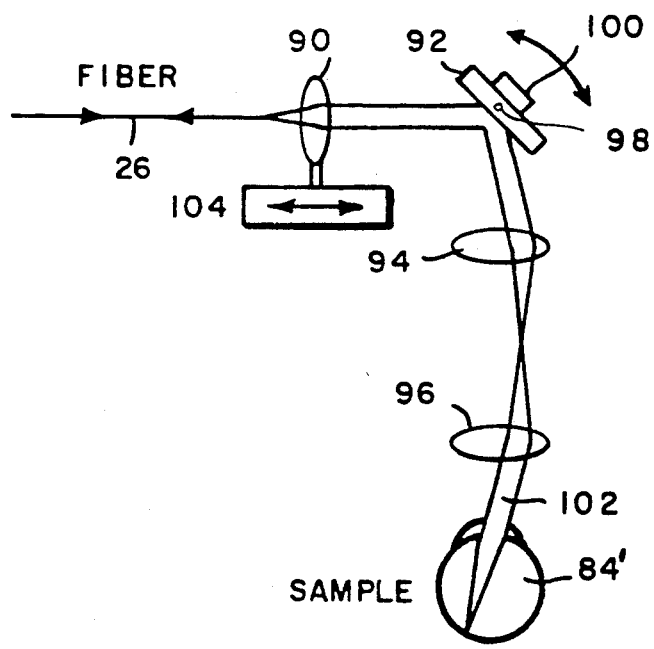
FIG. 3A is a diagram to an alternative probe module for performing two or three dimensional scanning.

FIG. 3A shows another embodiment of the invention wherein the probe module includes a first collimating lens 90, a steering mirror 92 which may be rotated by a galvanometer or other suitable mechanism 100 about one or two axes in a plane sometimes referred to as the pupil plane, and two additional focusing lenses 94 and 96. The sample is illustrated as an eye 84'. For FIG. 3A, focus is at or near the rear of eye 84' and the beam is pivoted about the nodal point of the eye at roughly the position of the ocular lens to scan different points along the rear surface of the eye as mirror 92 is rotated about pivot 98 and/or a pivot perpendicular thereto by mechanism 100. Again, the position of mirror 92, would be communicated to computer 72 in a suitable manner.

Further, as previously discussed, as corner cube 42 is moved by mechanism 46, the longitudinal or depth point in eye 84' at which detection occurs is varied. However, as is seen in FIG. 3A, the depth of the focal point for the light beam 102 in the eye remains constant. Thus, for much of a given depth scan, the beam 102 is out of focus with the point at which readings are being taken. To overcome this problem, a scanning mechanism 104 is provided which is synchronized with scanning mechanism 46 and which moves focusing lens 90 in a direction parallel to the direction of the light passing therethrough. This causes a change in the focal depth for beam 102 in sample 84'. With drives 46 and 104 synchronized, the focal point of beam 102 in eye 84' can be made substantially equal to the point being scanned in the eye at each point in time, providing optimum resolution for measuring and imaging. Other techniques known in the art for altering focal point in the longitudinal direction could also be utilized to synchronize the focal and detection points.

Figure 3B:
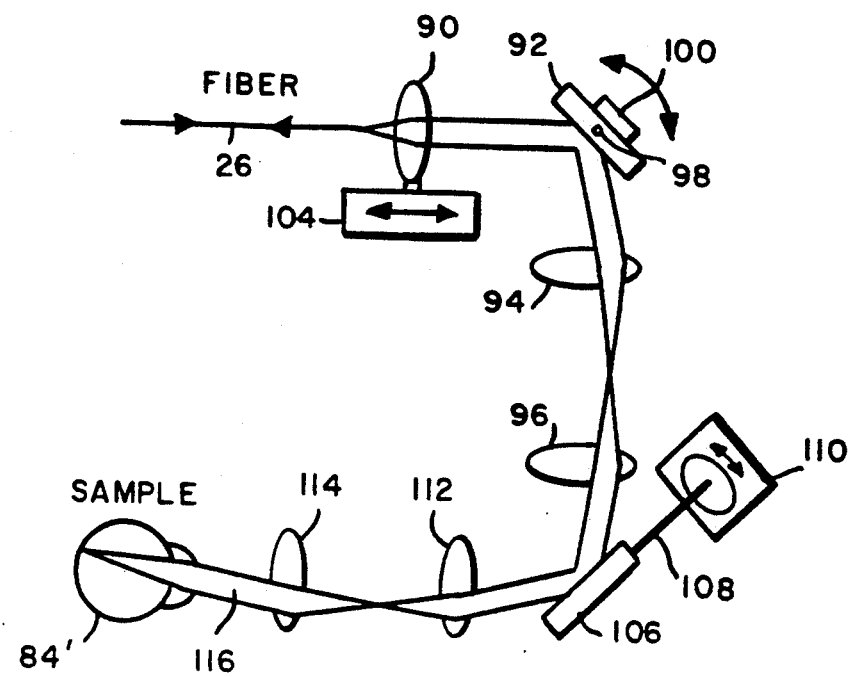
FIG. 3B is a diagram of an alternative probe module for achieving three dimensional scanning.

In FIG. 3A, scanning is provided in one or two transverse dimensions in a single pupil plane. FIG. 3B shows an embodiment wherein two single-axes scanning mirrors are used, an additional scanning mirror 106 being provided in a second pupil plane, which mirror is scanned about a shaft 108 by a galvanometer or other suitable mechanism 110 in a direction perpendicular to the direction of rotation of mirror 92. Light reflected off of mirror 106 is passed through lenses 112 and 114 to pass through the aperture of eye 84' to a selected focal point in the eye, which point may be varied in three dimensions. The galvanometer-driven mirrors 92 and 106 in FIGS. 3A and 3B could be replaced by rotating polygonal mirrors or other angular beam steering devices. As with prior embodiments, information concerning positions is communicated to computer 72 to permit proper imaging and processing.

Figure 3C:
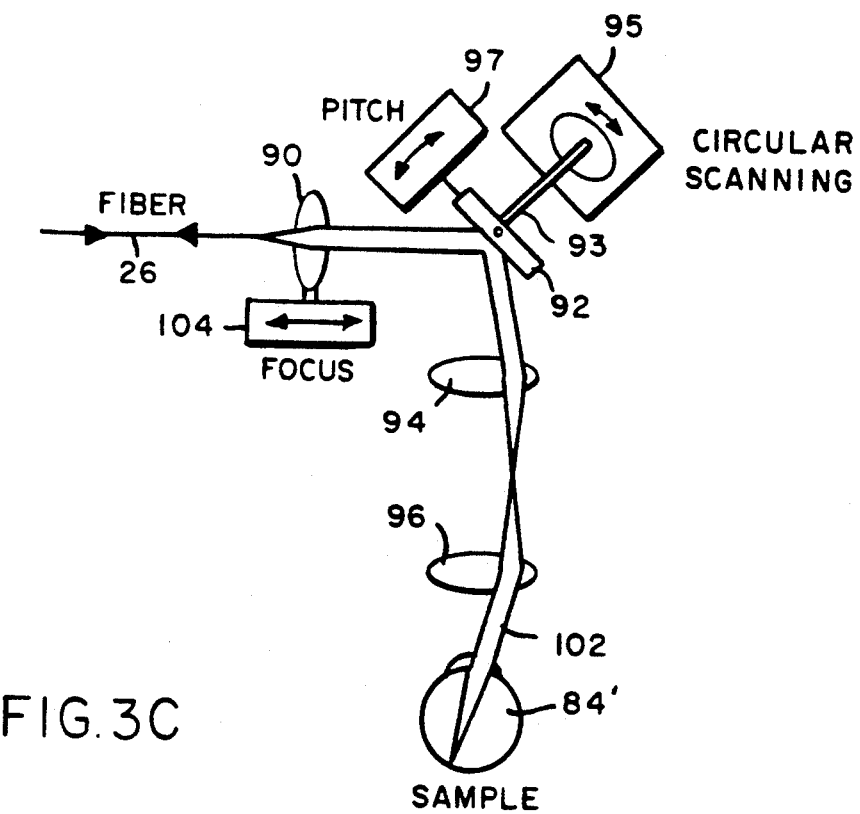
FIG. 3C is a diagram of an alternative probe module for performing circular scanning.

FIG. 3C shows still another embodiment of the assembly 25 wherein the mirror 92 in the pupil plane is rotated about a shaft 93 by a suitable rotary motion mechanism 95 and also has its pitch altered by a pitch altering mechanism 97. This results in a circular scan of eye 84', the size (i.e. diameter) of the circle being scanned depending on the pitch angle of mirror 92. The mechanism of FIG. 3C may for example be utilized to scan around the optic nerve head of the patient's eye and this scan may be processed to provide a two-dimensional scan. Although mechanical steering mechanisms have been discussed above, electro-optic steering mechanisms known in the art could also be utilized.

Figure 4A:
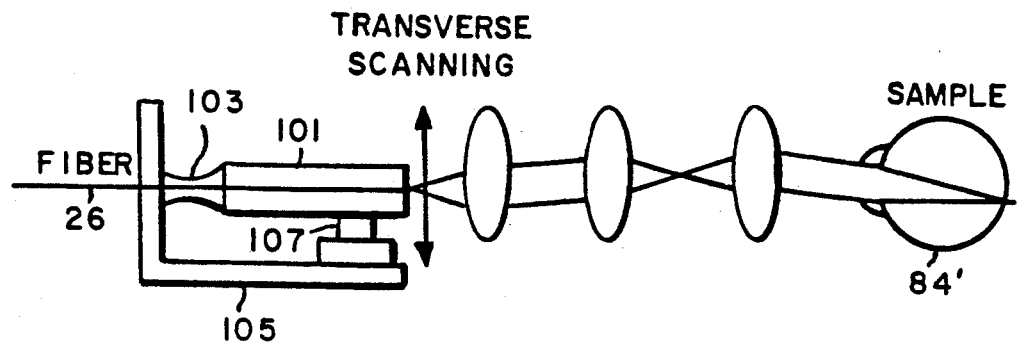
FIGS. 4A and 4B are diagrams of two additional probe module embodiments for performing multidimensional scanning.
Figure 4B:
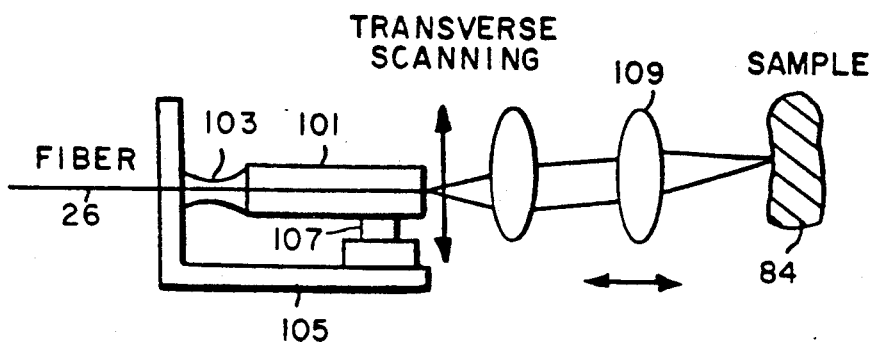

FIGS. 4A and 4B show still another embodiment for assembly 28 wherein fiber 26 is embedded in a sheath 101 which is attached to a stationary housing 105 through a pivot joint 103. Sheath 101 rests on a mechanism 107 fixed to housing 105 which mechanism may for example be a piezo electric crystal, stepper motor, electro-magnetic actuator, electro-static actuator, or the like. As mechanism 107 moves sheath 101, the tip of fiber 26 is moved transversely. This movement is converted by lenses to either an angular scan about a fixed entry point in eye 84' (FIG. 4A) and hence a transverse scan at the focal plane of the eye, or a transverse scan along a sample such as sample 84 (FIG. 4B). Lens 109 is shown as being movable longitudinally in FIG. 4B to either control longitudinal scanning or to synchronize the focusing in sample 84 with a longitudinal scan being performed in one of the manners mentioned previously in conjunction with FIGS. 1A–1B. If desired, pivot 103 may be eliminated so that sheath 101 moves straight up and down as a result of the operation of mechanism 107 rather than moving in an angular direction.

Figure 5:
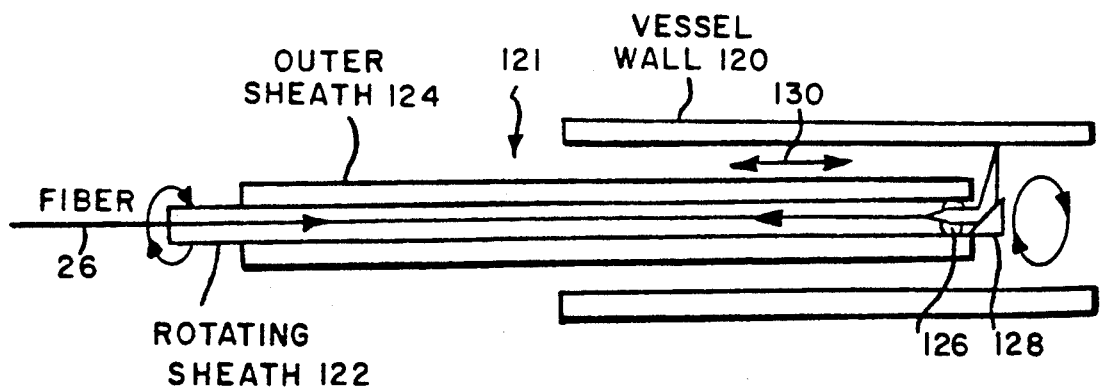
FIG. 5 is a side sectional side diagrammatic view of one embodiment of an endoscopic probe module.

FIG. 5 illustrates an alternative embodiment wherein the probe module is part of an angioscope or endoscope which may be utilized for imaging tubular structures 120 such as blood vessels, the esophagus, or the like. The distal end of fiber 26 is embedded in an inner sheath 122 which is rotatably mounted within an outer sheath 124. Inner sheath 122 has a lens 126 formed therein at the distal end of fiber 26 and terminates in an angled mirrored surface 128, which surface extends beyond the end of outer sheath 124. The probe module 121 may be moved laterally along vessel wall 120 (i.e. in the direction of arrow 130) either manually or by a suitable drive mechanism to scan the vessel wall in one dimension, and inner sheath 122, including mirror 128 which forms part thereof may be rotated relative to outer sheath 124 to scan the vessel wall in a second dimension. The movement of corner cube 42 under control of mechanism 46 causes scanning in the depth dimension of the vessel wall to provide three-dimensional scanning, or such scanning in the depth dimension may be achieved by one of the techniques described above. Since for the embodiment shown in FIG. 5, probe module 121 may move a substantial distance in the direction 130 along the vessel wall, in order to maintain the desired equal length for paths 26 and 30, fiber 26 may initially be provided with a certain amount of slack or may be curled or coiled to permit movement in this direction.

Figure 6:
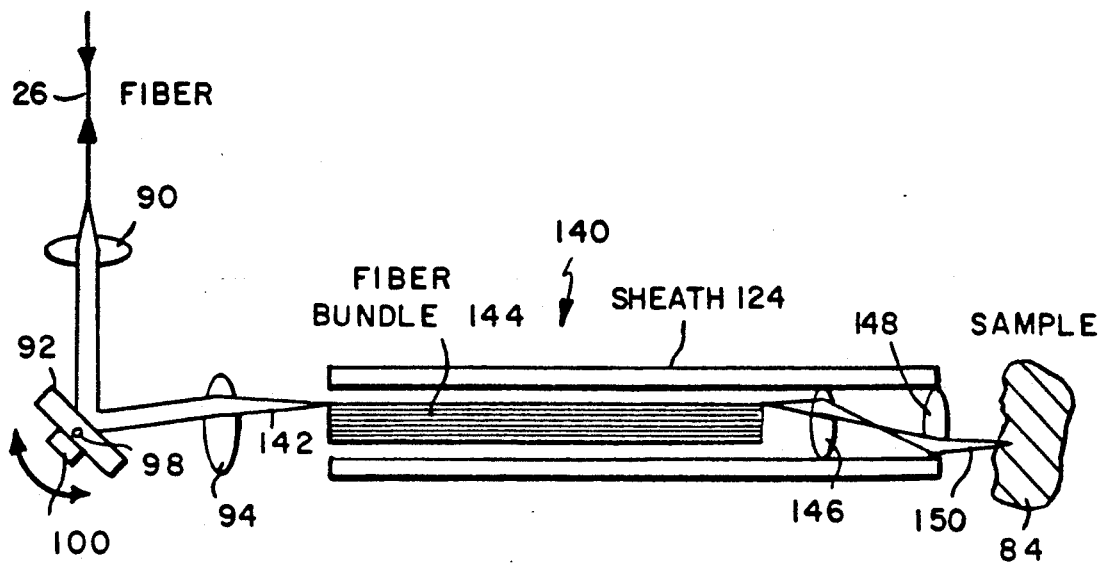
FIG. 6 is a side sectional diagrammatic view of a second embodiment of endoscopic probe module.

The endoscope probe 140 shown in FIG. 6 has a lens 90 at the distal end of fiber 26, a galvanometer-controlled mirror 92 and a focusing lens 94 which function in the same way and perform substantially the same functions as the corresponding elements in FIG. 3A. Output beam 142 from lens 94 is applied to a selected one or more of the single-mode optical fibers in fiber optic bundle 144. The fiber of bundle 144 to which beam 142 is applied depends on the scan position of mirror 92. At the distal end of fiber bundle 144, the output from the bundle 144 is passed through lenses 146 and 148 to sample 84. The transverse position of the scanning beam 150 on sample 84 varies with the fiber in bundle 144 to which beam 142 is applied and thus with the position of mirror 92. Beam 150 may thus be linearly scanned across sample 84 by the rotation of mirror 92. If mirror 92 is scanned in two dimensions, or if the output from lens 112 of the three-dimensional scanning mechanism of FIG. 3B is used instead of the output from lens 94, and fiber optic bundle 144 has fibers in two dimensions rather than in a single dimension, beam 150 may be scanned in a two-dimensional pattern across the surface of sample 84, permitting three-dimensional scanning to be performed.

Figure 7:
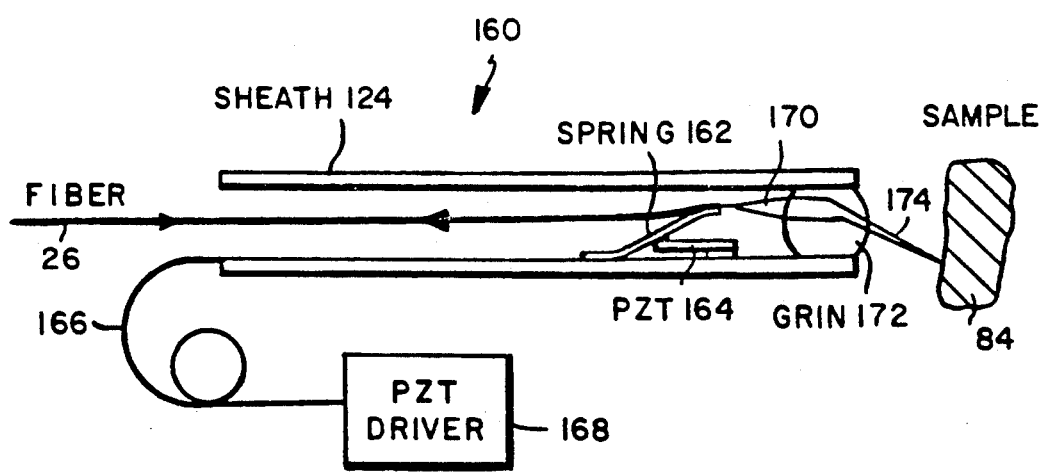
FIG. 7 is a side sectional diagrammatic view of a third embodiment of endoscopic probe module.

FIG. 7 shows still another endoscopic probe module 160 which may be constructed utilizing the teachings of this invention. For this embodiment, the distal end of fiber 26 is connected by a spring 162 to the inner wall of sheath 124. Spring 162 rests on and is vibrated by a piezoelectric transducer 164, or other electromagnetic, electrostatic or other actuator known in the art, which is connected by electric cable 166 running along the wall of sheath 124 to a driver 168. Transverse motion of fiber 26 causes a corresponding transverse movement of light beam 170 which is applied to a graded refractive index lens (GRIN lens) or other suitable lens 172. The output light beam 174 from lens 172 provides a transverse scan of sample 84.

While three different configurations of angioscopic-/endoscopic probes are shown in FIGS. 5–7, it is apparent that the teachings of this invention may be utilized to provide other angioscopic/endoscopic probe modules with either internal or external optics, with movement of either the fiber itself or of an external lens or mirror, and with varying scan patterns depending on application.

As was discussed earlier, a typical scan pattern for the various embodiments of the invention is for the probe assembly to be positioned at a selected transverse position with respect to the sample and mechanism 46 or other longitudinal scanning mechanism discussed in conjunction with FIGS. 1A–1B to be operated to complete the longitudinal or depth scan at the given transverse position. The transverse position is then altered in a manner, for example, described in conjunction with FIGS. 2–7 and a depth scan is completed at the new transverse position. This process is repeated until scanning has been performed at all desired transverse positions. This is the scan pattern illustrated in FIG. 8A.

Figure 8A:
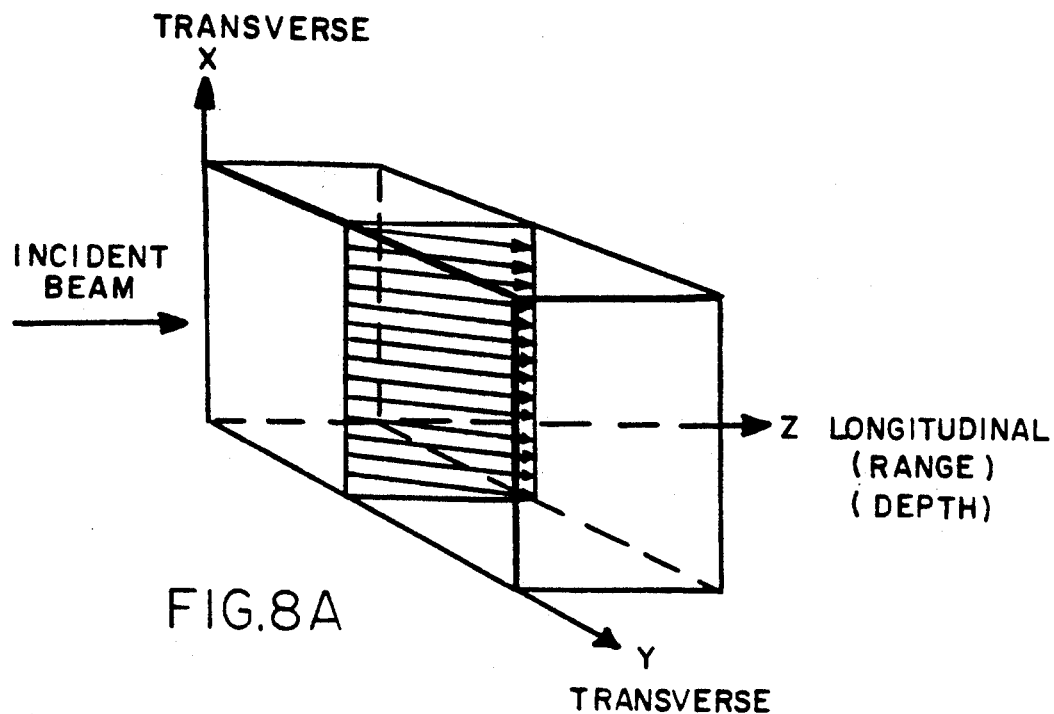
FIG. 8A is a diagram illustrating a first scan pattern for two dimensional scanning of a sample in accordance with the teachings of this invention.
Figure 8B:
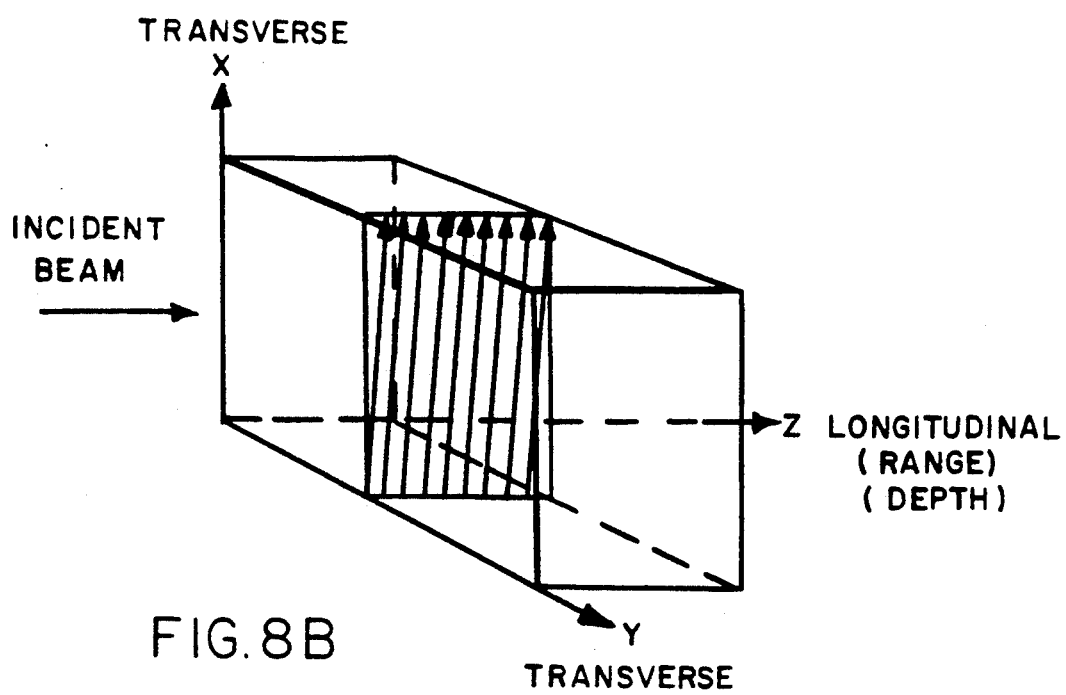
FIG. 8B is a diagram illustrating a second scan pattern for two dimensional scanning of a sample in accordance with the teachings of this invention.

However, the scan pattern shown in FIG. 8A requires high velocity longitudinal scanning. As discussed above, for some embodiments this longitudinal scanning is preferably at a constant velocity in order to produce a uniform Doppler shift which can be demodulated in circuit 56 (FIG. 1A). However, very high speed constant velocity scanning is difficult to achieve. Therefore, since there is less of a requirement on constant velocity for transverse scanning, and since resonantly driven galvanometers or fiber deflectors can be used to produce very high rates of transverse scanning, a scan pattern such as that shown in FIG. 8B may be preferable, particularly when a large number of transverse points are being utilized for the image. In FIG. 8B, a complete transverse scan is performed for each longitudinal position. In other words, referring, for example, to FIG. 2, mechanism 86 would perform a complete cycle for each position of mechanism 46 (FIG. 1A). With this scan pattern, mechanism 46 could be stepped rather than continuously slewed.

Figure 8C:
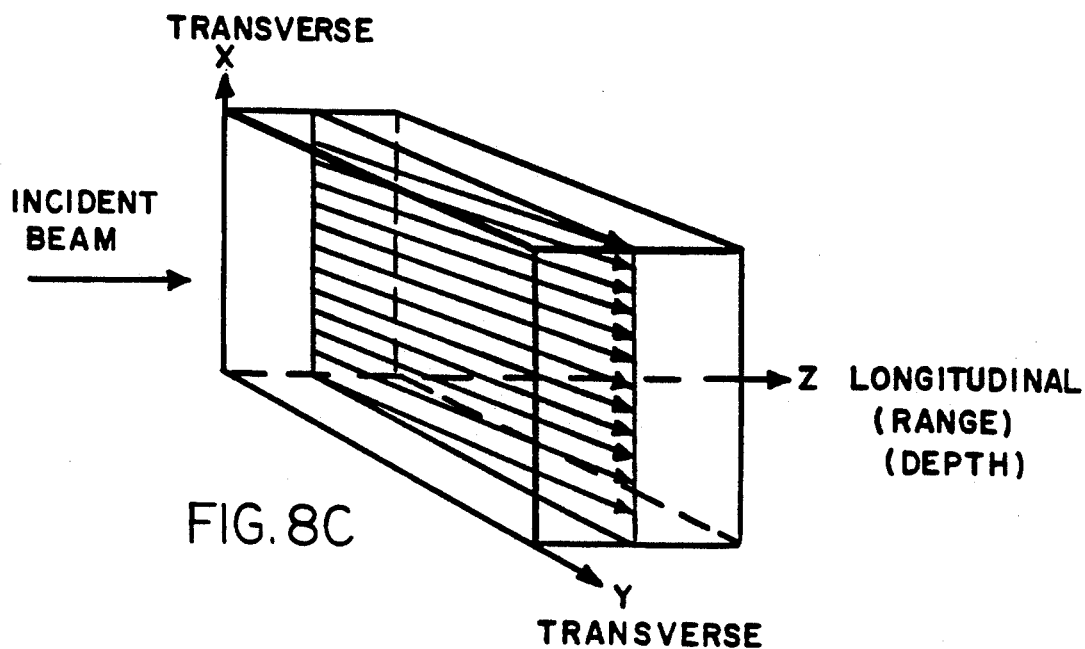
FIG. 8C is a diagram illustrating a third scan pattern for two dimensional scanning of a sample in accordance with the teachings of this invention.

FIG. 8C shows still another scan pattern which may be utilized in practicing the teachings of this invention. In this scan pattern, the longitudinal position in the sample is controlled using one of the techniques for longitudinal positioning previously discussed, for example by stepping the position of end mirror 44 to a selected position, and scanning is then performed at this depth or longitudinal position in the sample in one or two transverse dimensions. Once such a scan has been completed, the scan may either be repeated at the same depth or the longitudinal position control may be stepped to cause the subsequent scan to be performed at a different depth. It should be noted that this three dimensional scan is similar to that of FIG. 8B except that scanning at each depth level is performed in two rather than one dimension and such two dimensional scans may be performed at only one or more selected depths rather than at all selected depths.

In the foregoing description, the scan pattern in the transverse dimensions need not be performed using straight lines. Curved or circular scan patterns may be used in instances where it is desired to obtain depth and cross-sectional image information along specific surfaces which are not curved. The scanning embodiments of FIGS. 3C and 5 illustrate this point.

Figure 9:
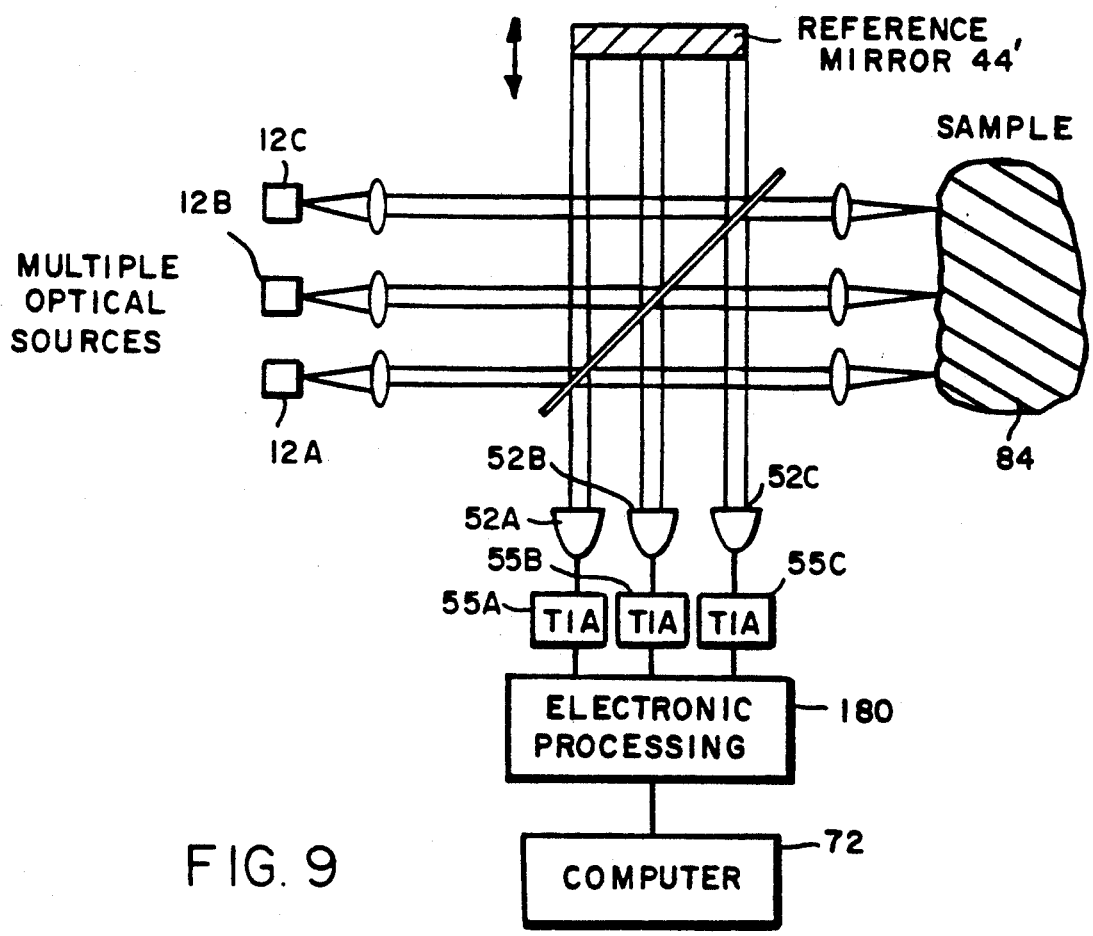
FIG. 9 is a schematic block diagram of a parallel scanned embodiment.

One potential difficulty with the embodiments of the invention discussed up to this point is that a complete two or three-dimensional scan of a sample may take a substantial period of time. While this may be acceptable for samples which do not change with time, such as certain mechanical or semiconductor samples, it may not be acceptable for biological samples which may change rapidly with time. FIG. 9 illustrates an alternative embodiment of the invention wherein this problem is overcome by scanning the sample in parallel using multiple optical sources 12A-12C and multiple detectors 52A-52C, but a single movable reference mirror 44'. Separate optical sources may be provided for each source 12A-12C or optical radiation from one or more sources may be divided to provide the desired number of optical sources. Similarly, multiple references may be provided. The outputs from the multiple detectors 52A-52C are processed by a special processing circuit 180 before being applied to computer 72. Where a small number of parallel scans are being performed, it may still be necessary to also scan such sources laterally. For example, each of the beams applied to sample 84 in FIG. 9 could also be scanned in the direction in and out of the figure to provide three-dimensional scanning. Alternatively, parallel scanning could be performed in three dimensions. Assuming the capacity of electronic processing circuitry 180 is adequate, a large enough number of parallel scans in two or three dimensions could be provided so that additional lateral or transverse scanning of the beams is not required. Parallel scanning could also be performed utilizing the scan technique of FIG. 1B.

Figure 10:
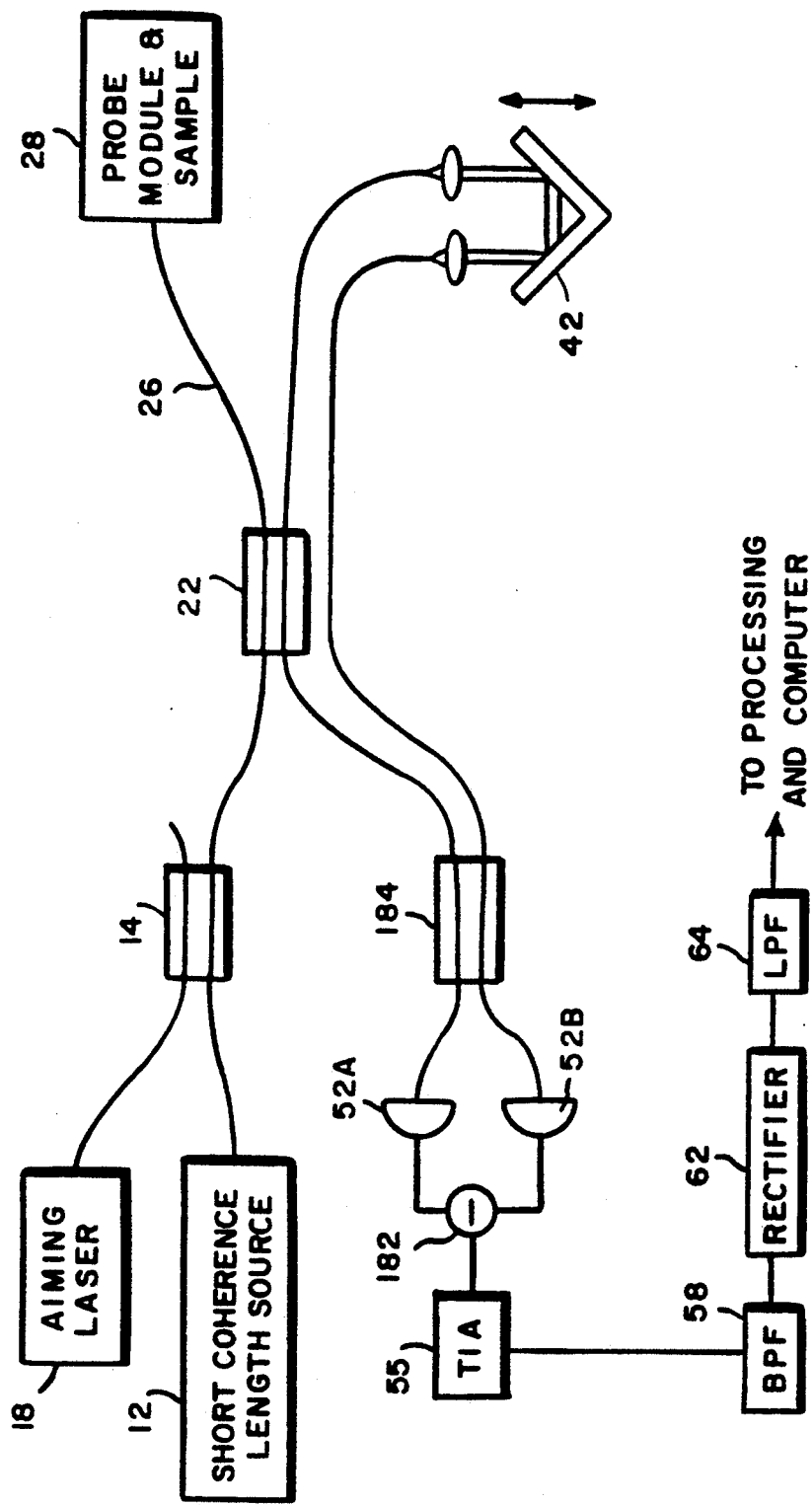
FIG. 10 is a schematic block diagram of a balanced receiver embodiment.

FIG. 10 illustrates one possible balanced receiver embodiment which may be utilized where excess intensity noise is present. For this embodiment, two photodetectors 52A and 52B are used in a manner known in the art to eliminate excess intensity noise, this noise being cancelled in subtraction circuit 182. With this embodiment, an additional optical coupler 184 is provided which receives input from reflections off the sample and two faces of corner cube 42. Numerous other techniques known in the art for performing balanced detecting might also be utilized. The operation for the embodiment of the invention shown in FIG. 10 is otherwise the same as that described for example in conjunction with FIG. 1A.

A potential problem for embodiments having the transverse scanning patterns is that, with the high transverse scanning rates the embodiments require, the signal bandwidths being employed may be so great that signal aliasing may occur in an image. Signal aliasing involves variation in image intensity for a given image which may, for example, vary at the Doppler shift frequency ($f_D$). One way of compensating for such aliasing is to perform multiple scans on a single sample, to store the results of each scan in memory 74 and to average the values from the various scans in computer 72 to eliminate the aliasing variations. Other preferred ways of eliminating aliasing are to use one of the techniques previously described to obtain a modulation higher than the signal bandwidth.

In the discussion above, it has been assumed that fiber optics are used for all optical paths. However, while fiber optics are normally preferred for this invention, bulk optics or other optical transmission techniques could be utilized for at least some of the optical paths in some applications.

Thus, while the invention has been particularly shown and described above with reference to various preferred embodiments, and numerous variations have been discussed for the embodiments, it is apparent that additional modifications, including the modifications discussed in the aforementioned copending application, the contents of which are incorporated herein by reference, could also be made in the invention by one skilled in the art without departing from the spirit and scope thereof.

What is claimed is:

1. A system for performing optical imaging on a sample comprising:

an optical radiation source;

a reference optical reflector;

a first optical path leading to said reflector;

a second optical path leading to said sample, said second optical path terminating in a probe module, said probe module including means for controlling the transverse position on said sample at which imaging is being performed, said sample position being selectively changed by said means for controlling to scan the sample in at least one transverse dimension;

means for applying optical radiation from said source through the first optical path to said reflector and through the second optical path including said probe module to the sample;

means for controlling the longitudinal range with the sample from which imaging information is being obtained;

means for combining reflections from the reflector received through the first optical path and reflections from the sample received through the second optical path, the resulting combined optical output having optical interference fringes;

means for detecting said output; and means for processing the detected output to obtain a selected image of the sample.

2. A system as claimed in claim 1 wherein said optical radiation source is a short coherence length optical source, wherein said means for controlling longitudinal range controls the relative lengths of said optical paths in accordance with a predetermined velocity profile having an instantaneous velocity V at each point on the profile, wherein interference fringes occur at length matched points on the two optical paths, and wherein said optical output has an instantaneous modulating frequency.

3. A system as claimed in claim 2 wherein said modulating frequency includes a Doppler shift frequency at a frequency $f_D \sim NV/\lambda$, where $\lambda$ is the wavelength of the radiation source.

4. A system as claimed in claim 1 wherein there is a bandwidth requirement to compensate for predominant low frequency noise for the system and for system, aliasing, wherein the velocity V is not sufficient to result in a Doppler shift frequency $f_D$ which is sufficient to meet said bandwidth requirement wherein said longitudinal range controlling means includes means for causing an additional modulation at a frequency $f_M$ for at least one of said optical paths, and wherein said means for processing includes a demodulator which demodulates for a modulating frequency which is a selected combination of $f_D$ and $f_M$.

5. A system as claimed in claim 4 wherein said additional modulation causing means includes at least one acousto-optic modulator (AOM) in at least one of said optical paths.

6. A system as claimed in claim 5 wherein there are two AOM's in said at least one path with $f_M$ being the difference frequency shift caused by said AOM's.

7. A system as claimed in claim 1 wherein said transverse position controlling means includes means for moving a probe module at the end of the said second optical path in at least one dimension substantially perpendicular to the direction in which optical radiation is applied to the sample.

8. A system as claimed in claim 7 wherein said means for moving moves the probe in two directions perpendicular to the direction of optical radiation.

9. A system as claimed in claim 1 wherein said probe module includes means for directing the optical radiation at a transverse position on the sample, and wherein said transverse position controlling means includes means for optically changing said transverse position in at least one dimension generally perpendicular to the direction in which the optical radiation is applied to the sample.

10. A system as claimed in claim 9 wherein said means for optically changing changes the transverse position in two directions perpendicular to the direction for optical radiation.

11. A system as claimed in claim 9 wherein said means for optically changing includes at least one movable mirror in the optical path of the radiation for steering the radiation at an angle dependent on mirror position.

12. A system as claimed in claim 11 wherein said at least one mirror is movable in two orthogonal directions for steering the radiation in a direction which varies in two dimensions.

13. A system as claimed in claim 11 wherein there are two mirrors successively spaced along said optical path, said mirrors being movable in different generally orthogonal directions.

14. A system as claimed in claim 9 wherein said means for optically changing includes at least one of an electro-optic or acousto-optic beam deflector.

15. A system as claimed in claim 9 including means for rotating said mirror for changing its pitch to effect circular scanning.

16. A system as claimed in claim 9 wherein said probe module is a mechanism for scanning internal channels.

17. A system as claimed in claim 16 wherein said probe module includes a rotating mirror for transversely directing the second optical path radiation.

18. A system as claimed in claim 17 wherein said probe module includes an outer sheath, an inner sheath rotatably mounted within said outer sheath, means for directing second optical path radiation through the inner sheath, and means movable with the inner sheath for focusing said radiation at a selected position on the internal channel, said selected position varying as the inner sheath is rotated.

19. A system as Claimed in claim 18 wherein said focusing means is a mirror mounted to rotate with said inner sheath and to reflect radiation passing through the inner sheath in a selected direction beyond an end of the outer sheath.

20. A system as claimed in claim 16 wherein said probe module includes an outer sheath, a bundle of optical fibers mounted in said sheath, means for optically connecting the second optical path to a first end of a selected one or more of said optical fibers, said means for optically connecting including means for controlling the optical fibers to which the second optical path is connected, and means for establishing a selected transverse position on the sample for each of said optical fibers and for optically connecting a second end of each optical fiber to the corresponding selected transverse position.

21. A system as claimed in claim 16 wherein said first and second optical paths are in the form of first and second optical fibers respectively; and wherein said probe module includes an outer sheath, means for securing a distal end of the second optical fiber to an inner wall of said sheath, said means including means for moving said distal end toward and away from said wall, and means for optically connecting said distal end to the sample, said means for optically connecting establishing a selected transverse position on the sample for each position of said distal end relative to said wall.

22. A system as claimed in claim 9 wherein said first and second optical paths are in the form of first and second optical fibers respectively; and wherein said transverse position controlling means includes means for translating the distal end of said second optical fiber.

23. A system as claimed in claim 1 wherein said longitudinal position controlling means includes means for controlling the length of the second optical path by controlling the spacing between the probe module and the sample.

24. A system as claimed in claim 1 wherein said longitudinal position controlling means includes means for periodically altering the length of the first optical path, resulting in periodic changes in the depth position in the sample for a length matched point of the second optical path; and wherein said probe module includes means for controlling the depth focus for the module in the sample so that the depth focus is maintained substantially at said length matched point as said point is periodically changed.

25. A system as claimed in claim 24 wherein said probe module includes at least one focusing lens for radiation received from said second optical path, and wherein said depth focus controlling includes means for moving a focusing lens in the direction of the radiation passing therethrough to control focus depth.

26. A system as claimed in claim 1 wherein the rates at which said longitudinal position controlling means and said transverse position controlling means are moved are such that points at all longitudinal ranges of interest are scanned for a given transverse position on the sample before the transverse position controlling means causes the probe module to initiate scanning at a new transverse position.

27. A system as claimed in claim 1 wherein the rates at which said longitudinal position controlling means and said transverse position controlling means are moved are such that points at all transverse positions to be scanned in at least one dimension are scanned at a given longitudinal range in the sample before the longitudinal position controlling means causes scanning at a new longitudinal range to be performed.

28. A system as claimed in claim 1 wherein said transverse position controlling means includes means for performing a two dimensional transverse scan at a longitudinal position in the sample determined by said longitudinal position controlling means.

29. A system as claimed in claim 1 wherein images taken during a given scan of the sample through all longitudinal ranges and transverse positions may have spurious intensity variations; and
including means for performing a plurality of scans on said sample, and means for averaging said scans to compensate for said intensity variations.

30. A system as claimed in claim 1 wherein said sample is a biological sample.

31. A system as claimed in claim 1 wherein said source is frequency modulatable spectrally coherent optical source, wherein said longitudinal position controlling means includes means for modulating the frequency of the source output, said interference resulting in a signal having a frequency proportional to the difference between the first an second path lengths, and wherein said means for processing includes means for converting said signal into imaging information.

32. A system as claimed in claim 1 including a plurality of first and second optical paths, there being an optical radiation source at the proximal end of each path, a reference reflector at the distal end of each first optical path, and a transverse point on the sample at the distal end of each second optical path, and wherein said means for processing includes means for processing the received images from the plurality of paths to effect parallel scanning of the sample.

33. A system as claimed in claim 1 including a balanced receiver for cancelling intensity noise.

34. A system for performing optical imaging on a sample comprising:
an optical radiation source;
an optical path leading to said sample, said optical path terminating in a probe module, said probe module including means for controlling the transverse position on said sample at which imaging is being performed, said sample position being selectively changed by said means for controlling to scan the sample in at least one transverse direction;
means for applying optical radiation through the optical path including the probe module to the sample;
means for controlling an optical characteristic of the radiation source output to control the longitudinal range within the sample from which imaging information is being obtained;
means for receiving optical reflections from said sample and responsive at least in part to said received reflections for generating an output having a frequency proportional to the length of the optical path to the longitudinal range in the sample being imaged;
means for detecting said output; and
means for processing the detected output to obtain a selected image of the sample.

35. A system as claimed in claim 34 wherein said optical radiation source is a frequency modulatable source, wherein said optical characteristic controlling means controls an input to the source to modulate its output frequency, and including a reference optical reflector, and an additional optical path leading to said reflector, and wherein said means for receiving receives reflections from said sample and said reflector and includes means for combining said reflections to generate interference fringes and an output having a frequency which is a function of the difference in such path lengths.

36. A system for performing optical imaging and measurements on a sample comprising:
a short coherence length optical radiation source;
a reference optical reflector;
a first optical path leading to said reflector;
a second optical path leading to said sample;
means for applying optical radiation from said source through the first optical path to said reflector and through the second optical path to the sample;
means for altering the length of the second optical path to alter in the relative lengths of said optical paths in accordance with a predetermined velocity profile, having an instantaneous velocity V at each point on the profile;
means for combining reflections from the reflector received through the first optical path and reflections from the sample received through the second optical path, the resulting combined optical output having interference fringes at length matched points on the two paths, the means for altering causing periodic changes in the longitudinal range position in the sample for the length matched points of the second optical path;
a probe module terminating said second optical path, said probe module including means for controlling the longitudinal range focus for the module in the sample so that the longitudinal range focus is maintained substantially at said length-matched point as said point is periodically changed;
means for detecting said output; and
means for processing the detected output to obtain a selected image of the sample.

37. A system as claimed in claim 36 wherein said probe module includes at least one focusing lens for radiation received from said second optical path, and wherein said longitudinal range controlling means includes means for moving a focusing lens in the direction of the radiation passing therethrough to control longitudinal range.

38. A system for performing optical imaging on a sample comprising:
- at least one optical radiation source;
- at least one optical reflector;
- a plurality of first optical paths leading from said at least one source to said at least one reflector;
- a plurality of second optical paths leading from said at least one source to selected transverse points on said sample;
- means for combining reflections from the at least one reflector received through each first optical path with reflections from the sample received through a corresponding second optical path, each resulting combined optical output having interference fringes at matched points on the two paths; and
- means for processing the combined optical outputs to obtain a plurality of images of the sample in parallel, said means including means for detecting each of said outputs and means for processing the detected outputs.

39. A system as claimed in claim 38 including an optical radiation source for each first optical path/second optical path pair.

40. A method for performing optical imaging on a sample comprising the steps of:
- (a) causing short coherence length optical radiation to impinge on a reference reflector and on the sample through first and second optical paths, respectively;
- (b) altering the relative lengths of said paths in accordance with a predetermined profile;
- (c) selectively changing the transverse position on the sample at which scanning is being performed;
- (d) combining reflections from the reflector received through the first optical path and reflections from the sample received through the second optical path, the resulting combined optical output having interference fringes at length matched points on the two paths;
- detecting said output; and
- processing the detected output to obtain a selected image of the sample.

41. A method as claimed in claim 40 wherein the relative rates at which altering step (b) and changing step (c) are performed are such that points at all longitudinal ranges of interest are scanned for a given transverse sample position before the transverse position is changed to initiate scanning at a new transverse position.

42. A method as claimed in claim 40 wherein the relative rates at which altering step (b) and changing step (c) are performed are such that points at all transverse positions to be scanned in at least one dimension are scanned at a given longitudinal range in the sample before the longitudinal range is altered to cause sampling at a new longitudinal range to be performed.

43. A method as claimed in claim 40 wherein the changing step (c) includes the step of performing a two-dimensional transverse scan at a longitudinal range in the sample determined by said altering step.

44. A method as claimed in claim 40 wherein said imaging involves non-invasive cross-sectional imaging in biological specimens.

45. A method as claimed in claim 44 wherein said cross-sectional imaging is performed on various eye sections.

46. A method as claimed in claim 40 wherein measurements taken during a given scan of the sample through all longitudinal ranges and transverse positions may have spurious intensity variations; and
- including the steps of performing a plurality of scans on said sample, and averaging said scans to compensate for said intensity variations.

* * * * *

UNITED STATES PATENT AND TRADEMARK OFFICE
CERTIFICATE OF CORRECTION

PATENT NO. : 5,321,501
DATED : June 14, 1994
INVENTOR(S) : Eric A. Swanson; David Huang; James G. Fujimoto; Carmen A. Puliafito; Charles P. Lin; Joel S. Schuman It is certified that error appears in the above-indentified patent and that said Letters Patent is hereby corrected as shown below:

Please insert the following paragraph in Column 1, line 11, after Field of the Invention:

--This invention was made with government support under Contract Nos. F19628-90-C-0002 by the Air Force, and N00014-86-K-0017 by the Navy, and Grant No. GM35459 by the National Institutes of Health. The government has certain rights in the invention.--

Signed and Sealed this

Fourth Day of October, 1994

Attest:

BRUCE LEHMAN

Attesting Officer

Commissioner of Patents and Trademarks

US005321501C1

(12) EX PARTE REEXAMINATION CERTIFICATE (5679th)
United States Patent
Swanson et al.

(10) Number: US 5,321,501 C1
(45) Certificate Issued: Feb. 27, 2007

(54) METHOD AND APPARATUS FOR OPTICAL IMAGING WITH MEANS FOR CONTROLLING THE LONGITUDINAL RANGE OF THE SAMPLE

(75) Inventors: Eric A. Swanson, Acton, MA (US); David Huang, Cambridge, MA (US); James G. Fujimoto, Cambridge, MA (US); Carmen A. Puliafito, Weston, MA (US); Charles P. Lin, Somerville, MA (US); Joel S. Schuman, Wayland, MA (US)

(73) Assignee: Massachusetts Institute of Technology, Cambridge, MA (US)

Reexamination Request:
No. 90/006,816, Oct. 20, 2003

Reexamination Certificate for:
Patent No.: 5,321,501
Issued: Jun. 14, 1994
Appl. No.: 07/875,670
Filed: Apr. 29, 1992

Certificate of Correction issued Oct. 4, 1994.

Related U.S. Application Data

(63) Continuation-in-part of application No. 07/692,877, filed on Apr. 29, 1991, now abandoned.

(51) Int. Cl.
*G01B 9/02* (2006.01)

(52) U.S. Cl. .............. 356/479; 356/73.1; 250/227.27
(58) Field of Classification Search .............. 356/479, 356/497; 250/227.19, 2; 600/478
See application file for complete search history.

(56) References Cited

U.S. PATENT DOCUMENTS 4,928,005 A 5/1990 Lefévre et al. ........ 250/227.23
5,202,745 A 4/1993 Sorin et al. ................ 356/73.1

FOREIGN PATENT DOCUMENTS

GB 2 191 855 A 12/1987

OTHER PUBLICATIONS

R.C. Youngquist et al., "Optical coherence–domain reflectometry: a new optical evaluation technique," *Optics Letters*, vol. 12, No. 3, Mar. 1987, pp. 158–160.

K. Takada et al., "New measurement system for fault location in optical waveguide devices based on an interferometric technique," *Applied Optics*, vol. 26, No. 9, May 1, 1987, pp. 1603–1606.

B.L. Danielson et al., "Guided–wave reflectometry with micrometer resolution," *Applied Optics*, vol. 26, No. 14, Jul. 15, 1987, pp. 2836–2842.

A.F. Fercher et al., "Eye–length measurement by interferometry with partially coherent light," *Optics Letters*, vol. 13, No. 3, Mar. 1988, pp. 186–188.

P. Beaud et al., "Optical Reflectometry with Micrometer Resolution for the Investigation of Integrated Optical Devices," *IEEE Journal of Quantum Electronics*, vol. 25, No. 4, Apr. 1989, pp. 755–759.

(Continued)

*Primary Examiner*—Zandra V. Smith

(57) ABSTRACT

A method and apparatus for performing optical imaging on a sample wherein longitudinal scanning or positioning in the sample is provided by either varying relative optical path lengths for an optical path leading to the sample and to a reference reflector, or by varying an optical characteristic of the output from an optical source applied to the apparatus. Transverse scanning in one or two dimensions is provided on the sample by providing controlled relative movement between the sample and a probe module in such direction and/or by steering optical radiation in the probe module to a selected transverse position. The probe module may be an external module or may be an endoscope or angioscope utilized for scanning internal channels. Multiple optical paths may be provided for parallel scanning and focus may be enhanced by varying the focal point in the sample in synchronism with longitudinal scanning of the sample.

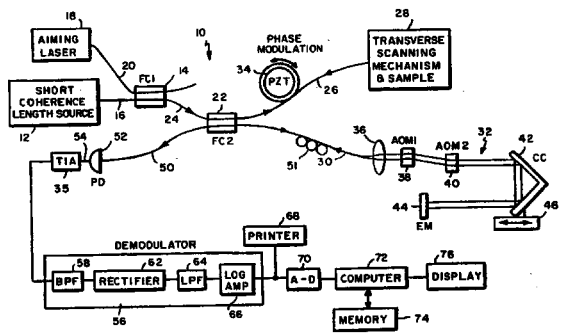
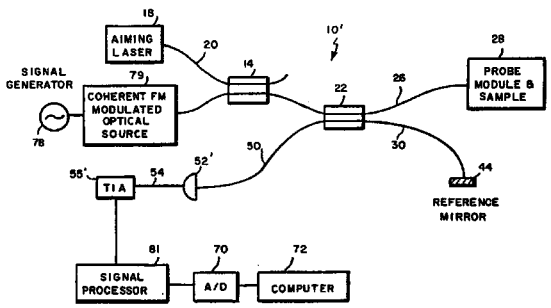

OTHER PUBLICATIONS

H.H. Gilgen et al., "Submillimeter Optical Reflectometry," *Journal of Lightwave Technology*, vol. 7, No. 8, Aug. 1989, pp. 1225–1233.

M. Tateda et al., "Water Penetration Sensing Using Wavelength Tunable OTDR*," *IEEE Photonics Technology Letters*, vol. 3, No. 1, Jan. 1991, pp. 1–3.

C.K. Hitzenberger, "Optical Measurement of the Axial Eye Length by Laser Dopler Interferometry," *Investigative Ophthalmology & Visual Science*, vol. 32, No. 3, Mar. 1991, pp. 616–624.

M. Kobayashi et al., "Polarization–Independent Interferometric Optical–Time–Domain Reflectometer," *Journal of Lightwave Technology*, vol. 9, No. 5, May 1991, pp. 623–628.

M. Kobayashi et al., "Optical Fiber Component Characterization by High–Intensity and High–Spatial–Resolution Interferometric Optical–Time–Domain Reflector," *IEEE Photonics Technology Letters*, vol. 3, No. 6, Jun. 1991, pp. 564–566.

K. Takada et al., "Rayleigh backscattering measurement of single–mode fibers by low coherence optical time–domain reflectometer with 14 μm spatial resolution," *Appl. Phys. Lett.*, vol. 59, No. 2, Jul. 8, 1991, pp. 143–145.

K. Takada et al., "Resolution Control of Low–Coherence Optical Time–Domain Reflectometer Between 14 and 290 μm," *IEEE Photonics Technology Letters*, vol. 3, No. 7, Jul. 1991, pp. 676–678.

D. Huang et al., "Micron–Resolution Ranging of Cornea Anterior Chamber by Optical Reflectometry," *Lasers in Surgery and Medicine*, vol. 11 (1991), pp. 419–425.

K. Takada et al., "Phase–noise and shot–noise limited operations of low coherence optical time domain reflectometry," *Appl. Phys. Lett.*, vol. 29, No. 20, Nov. 11, 1991, pp. 2483–2485.

D. Huang et al., "Optical Coherence Tomography," *Science*, vol. 254, Nov. 22, 1991, pp. 1178–1181.

X. Clivaz et al., "High–resolution reflectometry in biological tissues," *Optics Letters*, vol. 17, No. 1, Jan. 1, 1992, pp. 4–6.

W.V. Sorin et al., "Simultaneous Thickness and Group Index Measurement Using Optical Low–Coherence Reflectometry," *IEEE Photonics Technology Letters*, vol. 4, No. 1, Jan. 1992, pp. 105–107.

E.A. Swanson et al., "High–speed optical coherence domain reflectometry," *Optics Letters*, vol. 17, No. 2, Jan. 15, 1992, pp. 151–153.

C.K. Hitzenberger et al., "Measurement of Corneal Thickness by Laser Doppler Interferometry," *Investigative Ophthalmology & Visual Science*, vol. 33, No. 1, Jan. 1992, pp. 98–103.

M. Davidson et al., "An application of interference microscopy to integrated circuit inspection and metrology," *Proceedings of SPIE—The International Society for Optical Engineering*, vol. 775, Mar. 4–6, 1987, pp. 233–241.

H. Park et al., "High resolution optical ranging system," *Applied Physics*, vol. 20, No. 14, Jul. 15, 1981, pp. 2389–2394.

D. Huang, "Optical Coherence Tomography," *Science*, vol. 254, Nov. 22, 1991, pp. 1178–1181.

A.J. den Boef, "Two–wavelength scanning spot interferometer using single–frequency diode lasers," *Applied Optics*, vol. 27, No. 2, Jan. 15, 1988, pp. 306–311.

US 5,321,501 C1

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claims 1–46 is confirmed.

New claims 47–247 are added and determined to be patentable.

47. *A system as claimed in claim 1, wherein the image of the sample includes gray scale levels to indicate characteristics of the sample.*

48. *A system as claimed in claim 1, wherein the image of the sample includes a color spectrum to indicate characteristics of the sample.*

49. *A system as claimed in claim 1, wherein said means for controlling the transverse scanning on the sample includes a movable mirror.*

50. *A system as claimed in claim 49, wherein the movement of the movable mirror is controlled by a galvanometer.*

51. *A system as claimed in claim 1, wherein said means for controlling the transverse scanning on the sample includes a pair of movable mirrors to scan the radiation in orthogonal directions.*

52. *A system as claimed in claim 1 wherein said means for controlling the transverse scanning on the sample includes a rotating polygonal mirror.*

53. *A system as claimed in claim 1, further including an endoscope for positioning the probe module with respect to the sample.*

54. *A system as claimed in claim 53, wherein the sample is a tubular structure within the body of a patient.*

55. *A system as claimed in claim 54, wherein the tubular structure is the esophagus.*

56. *A system as claimed in claim 54, wherein the tubular structure is the bronchial tree.*

57. *A system as claimed in claim 54, wherein the tubular structure is the urinary tract.*

58. *A system as claimed in claim 54 wherein the tubular structure is the genital tract.*

59. *A system as claimed in claim 1, further including an angioscope for positioning the probe module with respect to the sample.*

60. *A system as claimed in claim 59, wherein the sample is a blood vessel.*

61. *A system as claimed in claim 1, wherein said means for processing the detected output performs dynamic range compression.*

62. *The system as claimed in claim 61, wherein a logarithmic amplifier is utilized in performing the dynamic range compression.*

63. *A system as claimed in claim 61, wherein said processing means includes a computer and wherein the dynamic range compression is performed in the computer.*

64. *A system as claimed in claim 1, further including a second light source for generating a visible beam of radiation to facilitate alignment.*

65. *A system as claimed in claim 1, wherein at least one of said optical paths includes an optical fiber.*

66. *A system as claimed in claim 65, wherein at least one end of the optical fiber is angled polished.*

67. *A system as claimed in claim 65, wherein at least one end of the optical fiber includes an anti-reflection coating.*

68. *A system as in claim 1, wherein each of said first and second optical paths includes an optical fiber.*

69. *A system as claimed in claim 68, wherein at least one end of each optical fiber is angled polished.*

70. *A system as claimed in claim 69, wherein at least one end of each optical fiber includes an anti-reflection coating.*

71. *A system as claimed in claim 69, wherein the lengths of the fibers are substantially equal.*

72. *A system as claimed in claim 30, wherein the biological sample is the eye.*

73. *A system as claimed in claim 1, wherein said second optical path includes an optical fiber for transmitting optical radiation to the sample.*

74. *A system as claimed in claim 73, wherein a focusing element is located adjacent the end of the fiber.*

75. *A system as claimed in claim 74, further including an angled reflector positioned to redirect the focused optical radiation exiting the fiber towards the sample.*

76. *A system as claimed in claim 75, wherein the angled reflector is rotatable to scan the sample at angle with respect to the longitudinal axis of the fiber.*

77. *A system as claimed in claim 1, wherein the transverse scanning is performed at a selected longitudinal position.*

78. *A system as claimed in claim 77, wherein said transverse scanning is performed in one dimension at the selected longitudinal position.*

79. *A system as claimed in claim 77, wherein said transverse scanning is performed in two dimensions at the selected longitudinal position.*

80. *A system as claimed in claim 1, wherein said means controlling the longitudinal range within the sample from which imaging information is being obtained is operated in a step fashion to control the desired scan depth.*

81. *A system as claimed in claim 80 wherein said transverse scanning is performed in one dimension at a selected scan depth.*

82. *A system as claimed in claim 80, wherein said transverse scanning is performed in two dimensions at a selected scan depth.*

83. *A system as claimed in claim 1 wherein said transverse scanning is performed in one dimension at a selected scan depth.*

84. *A system as claimed in claim 1, wherein said transverse scanning is performed in two dimensions at a selected scan depth.*

85. *A system as claimed in claim 1, wherein the longitudinal range is controlled by mechanically moving a mirror.*

86. *A system as claimed in claim 85 wherein said mirror is moved at a velocity greater than 1 cm/sec.*

87. *A system as claimed in claim 1, wherein the longitudinal range is controlled by varying the optical frequency of the optical radiation.*

88. *A system as claimed in claim 1, wherein the longitudinal range is controlled electronically.*

89. *A system as claimed in claim 1, wherein longitudinal ranging information is obtained by optical frequency domain reflectometry.*

90. *A system as claimed in claim 1, further including a memory for storing the results of more than one scan of said sample.*

91. *A system as claimed in claim 90, wherein said processing means functions to average the results of the scans stored in said memory to improve the image.*

92. A system as claimed in claim 1, wherein said image is a non-invasive cross-sectional image of a biological specimen.

93. A system as claimed in claim 92, wherein said means for processing the detected output performs dynamic range compression and wherein said image includes one of gray scale levels or a color spectrum to indicate characteristics of the sample.

94. A system as claimed in claim 1, further including an optical material located in one of the optical paths for controlling group velocity dispersion.

95. A system as claimed in claim 94, wherein said optical material is selected to equalize the group velocity dispersion in each optical path.

96. A system as claimed in claim 1, further including a polarization controller located in one of the optical paths.

97. A system as claimed in claim 1, wherein the detected output includes a frequency that is proportional to the difference in optical path length between the sample and the reference reflector.

98. A system as claimed in claim 97, wherein the frequency is an RF frequency.

99. A system as claimed in claim 97, wherein the frequency information is converted into spatial information using a Fourier transform technique.

100. A system as claimed in 1, wherein said source is linearly chirped.

101. A system as claimed in 1, wherein said source is frequency modulated.

102. A system as claimed in 1, wherein said source is a short coherence length source.

103. A system as claimed in claim 1, wherein said source has a coherence length of less than 10 micrometers.

104. A system as claimed in claim 1, wherein the detecting means comprises multiple detectors.

105. A system as claimed in claim 104, wherein the output of the multiple detectors is used for scanning the sample in parallel.

106. A system as claimed in claim 1, wherein said first optical path includes a first portion wherein optical radiation is applied from the source to said reflector and a second portion separate from said first potion through which radiation reflected from the reflector travels to said combining means.

107. A system as claimed in claim 1, wherein the first optical path includes at least a common portion through which radiation travels to the reflector from the source and reflected radiation travels from the reflector to the combining means.

108. A system as claimed in claim 1, wherein said means for applying optical radiation from said source through the first and second optical paths includes a first beam splitter for splitting the radiation from the source along said first and second optical paths.

109. A system as claimed in claim 108, wherein said first beam splitter also functions as said combining means.

110. A system as claimed in claim 108, further wherein said combining means is a second beam splitter separate from said first beam splitter.

111. A system as claimed in claim 1, wherein said first optical path includes a retroreflector.

112. A system as claimed in claim 111, wherein said retroreflector is a corner cube.

113. A system as claimed in claim 1, wherein said detecting means includes a balanced receiver.

114. A system as claimed in claim 113, wherein said balanced receiver includes a pair of detectors.

115. A system as claimed in claim 1, wherein said processing means includes an analog to digital converter.

116. A system as claimed in claim 115, wherein said processing means uses the output of the analog to digital converter to generate an image that includes one of gray scale levels or a color spectrum to indicate characteristics of the sample.

117. A system as claimed in claim 1, wherein the detecting means generates a current varying electrical signal and further including a means for converting the current varying electrical signal into a voltage varying signal.

118. A system as claimed in claim 117, wherein said converting means is a transimpedance amplifier.

119. A system as claimed in claim 1, further including a transimpedance amplifier connected between said detecting means and said processing means.

120. A system as claimed in claim 1, wherein said processing means detects points of interest in the detected output to facilitate the generation of the image.

121. A system as claimed in claim 1, wherein said source is a short coherence length source and wherein each of said first and second optical paths includes an optical fiber and further including a polarization controller located in one of the optical paths and wherein said image includes one of gray scale levels or a color spectrum to indicate characteristics of the sample.

122. A system as claimed in claim 121, further comprising a first beam splitter for splitting the radiation from the source along said first and second optical paths.

123. A system as claimed in claim 122, wherein said first beam splitter also functions as said combining means.

124. A system as claimed in claim 121, wherein said processing means includes an analog to digital converter.

125. A system as claimed in claim 124, wherein the detecting means generates a current varying electrical signal and further including a means for converting the current varying electrical signal into a voltage varying signal.

126. A system as claimed in claim 124, wherein said processing means detects points of interest in the detected output to facilitate the generation of the image.

127. A method as claimed in claim 40, wherein the image of the sample includes gray scale levels to indicate characteristics of the sample.

128. A method as claimed in claim 40, wherein the image of the sample includes a color spectrum to indicate characteristics of the sample.

129. A method as claimed in claim 40, wherein the changing in step (c) includes scanning the optical radiation with a movable mirror.

130. A method as claimed in claim 129, wherein the movement of the movable mirror is controlled by a galvanometer.

131. A method as claimed in claim 40, wherein the changing in step (c) includes scanning the optical radiation with a pair of movable mirrors to scan the radiation in orthogonal directions.

132. A method as claimed in claim 40, wherein the changing in step (c) includes scanning the optical radiation with a rotating polygonal mirror.

133. A method as claimed in claim 40, wherein the step (a) includes using an endoscope to deliver the optical radiation to the sample.

134. A method as claimed in claim 133, wherein the sample is a tubular structure within the body of a patient.

135. A method as claimed in claim 134, wherein the tubular structure is the esophagus.

136. A method as claimed in claim 134, wherein the tubular structure is the bronchial tree.

137. A method as claimed in claim 134, wherein the tubular structure is the urinary tract.

138. A method as claimed in claim 134, wherein the tubular structure is the genital tract.

139. A method as claimed in claim 40, wherein step (a) includes using an angioscope to deliver the optical radiation to the sample.

140. A method as claimed in claim 139, wherein the sample is a blood vessel.

141. A method as claimed in claim 40, wherein the step of processing the detected output includes performing dynamic range compression.

142. A method as claimed in claim 141, wherein a logarithmic amplifier is utilized in performing the dynamic range compression.

143. A method as claimed in claim 40, further including the step of generating a separate visible beam of radiation and using that visible beam to facilitate alignment of the second optical path.

144. A method as claimed in claim 40, wherein at least one of said optical paths includes an optical fiber.

145. A method as claimed in claim 144, wherein at least one end of the optical fiber is angled polished.

146. A method as claimed in claim 144, wherein at least one end of the optical fiber includes an anti-reflection coating.

147. A method as in claim 40, wherein each of said first and second optical path includes an optical fiber.

148. A method as claimed in claim 147, wherein at least one end of each optical fiber is angled polished.

149. A method as claimed in claim 147, wherein at least one end of each optical fiber includes an anti-reflection coating.

150. A method as claimed in claim 147, wherein the lengths of the fibers are substantially equal.

151. A method as claimed in claim 40, wherein said sample is a biological sample.

152. A method as claimed in claim 151, wherein the biological sample is the eye.

153. A method as claimed in claim 40, wherein said second optical path includes an optical fiber for transmitting optical radiation to the sample.

154. A method as claimed in claim 153, wherein a focusing element is located adjacent the end of the fiber.

155. A method as claimed in claim 154, further including an angled reflector positioned to redirect the focused optical radiation exiting the fiber towards the sample.

156. A method as claimed in claim 155, further including the step of rotating said angled reflector to scan the sample at angle with respect to the longitudinal axis of the fiber.

157. A method as claimed in claim 40, wherein the step (b) is performed by mechanically moving a mirror.

158. A method as claimed in claim 40 wherein the step of processing the detected output includes performing dynamic range compression and wherein the image includes one of gray scale levels or a color spectrum to indicate characteristics of the sample.

159. A method as claimed in claim 40, further including the step of controlling the polarization in at least one of the optical paths.

160. A method as claimed in claim 40, wherein a beam splitter is used to divide the radiation along the first and second optical paths and the same beam splitter is used to combine the reflections from the reflector and the sample.

161. A method as claimed in claim 40 wherein said detecting step is performed using a balanced receiver.

162. A method as claimed in claim 40 wherein the processing step includes converting the detected output from an analog signal to a digital signal.

163. A method as claimed in claim 40, wherein the detected output is a current varying electrical signal and further including the step of converting the current varying electrical signal intor a voltage varying signal.

164. A method as claimed in claim 40, wherein each of said first and second optical paths includes an optical fiber and further including the step of controlling the polarization in at least one of the optical paths and wherein said image includes one of gray scale levels or a color spectrum to indicate characteristics of the sample.

165. A method as claimed in claim 164, wherein a beam splitter is used to divide the radiation along the first and second optical paths and the same beam splitter is used to combine the reflected optical signals from said optical paths.

166. A method as claimed in claim 165, wherein the processing step includes converting the detected output from an analog signal to a digital signal.

167. A method as claimed in claim 166, wherein the detected output is a current varying electrical signal and further including the step of converting the current varying electrical signal into a voltage varying signal.

168. A method as claimed in claim 166, further including the step of detecting points of interest in the detected ouput to facilitate the generation of the image.

169. A system for performing optical imaging on a sample comprising:

an optical radiation source;

a reference optical reflector;

a first optical path leading to said sample, said optical path terminating in a probe module, said probe module including means for controlling the transverse position on said sample at which imaging is being performed, said sample position being selectively changed by said means for controlling to scan the sample in at least one transverse direction;

a second optical path leading to said reflector;

means for applying optical radiation through the first optical path including the probe module to the sample and the second optical path to said reflector;

means for controlling an optical characteristic of the radiation source output to control the longitudinal range within the sample from which imaging information is being obtained;

means for receiving optical reflections from said sample and said reflector and responsive at least in part to said received reflections for generating an output having a frequency proportional to the difference in length of the two optical paths corresponding to the longitudinal range in the sample being imaged;

means for detecting said output; and means for processing the detected output to obtain a selected image of the sample.

170. A system as claimed in claim 169, wherein said means for controlling the optical characteristic of the radiation source modulates the frequency of output frequency of the source.

171. A system as claimed in claim 169, wherein the frequency modulation is in the form of an FM chirp.

172. A system as claimed in claim 169, wherein said source is linearly chirped.

173. A system as claimed in claim 169, wherein the image of the sample includes gray scale levels to indicate characteristics of the sample.

174. A system as claimed in claim 169, wherein the image of the sample includes a color spectrum to indicate characteristics of the sample.

175. A system as claimed in claim 169, wherein said means for controlling the transverse scanning on the sample includes a movable mirror.

176. A system as claimed in claim 175 wherein the movement of the movable mirror is controlled by a galvanometer.

177. A system as claimed in claim 169, wherein said means for controlling the transverse scanning on the sample includes a pair of movable mirrors to scan the radiation in orthogonal directions.

178. A system as claimed in claim 169, wherein said means for controlling the transverse scanning on the sample includes a rotating polygonal mirror.

179. A system as claimed in claim 169, further including an endoscope for positioning the probe module with respect to the sample.

180. A system as claimed in claim 179, wherein the sample is a tubular structure within the body of a patient.

181. A system as claimed in claim 180, wherein the tubular structure is the esophagus.

182. A system as claimed in claim 180, wherein the tubular structure is the bronchial tree.

183. A system as claimed in claim 180, wherein the tubular structure is the urinary tract.

184. A system as claimed in claim 180, wherein the tubular structure is the genital tract.

185. A system as claimed in claim 169, further including an angioscope for positioning the probe module with respect to the sample.

186. A system as claimed in claim 185, wherein the sample is a blood vessel.

187. A system as claimed in claim 169, further including a second light source for generating a visible beam of radiation to facilitate alignment.

188. A system as claimed in claim 169, wherein each of said first and second optical path includes an optical fiber.

189. A system as claimed in claim 188, wherein at least one end of each optical fiber is angled polished.

190. A system as claimed in claim 188, wherein at least one end of each optical fiber includes an anti-reflection coating.

191. A system as claimed in claim 169, wherein said sample is a biological sample.

192. A system as claimed in claim 191, wherein the biological sample is the eye.

193. A system as claimed in claim 169, further including a memory for storing the results of more than one scan of said sample.

194. A system as claimed in claim 193, wherein said processing means functions to average the results of the scans stored in said memory to improve the image.

195. A system as claimed in claim 169, wherein said image is a non-invasive cross-sectional image of a biological specimen.

196. A system as claimed in claim 169, wherein said means for applying optical radiation from said source through the first and second optical paths includes a first beam splitter for splitting the radiation from the source along said first and second optical paths.

197. A system as claimed in claim 196, wherein said first beam splitter also functions to combine the optical reflections from said sample and said reflector.

198. A system as claimed in claim 169, wherein said processing means includes an analog to digital converter.

199. A system for performing optical imaging on a sample comprising:

an optical radiation source;
a first optical path leading to said sample, said optical path terminating in a probe module, said probe module including means for controlling the transverse position on said sample at which imaging is being performed, said sample position being selectively changed by said means for controlling to scan the sample in at least one transverse direction;
a second optical path;
means for applying optical radiation through the first optical path including the probe module to the sample and the second optical path;
means for controlling an optical characteristic of the radiation source output to control the longitudinal range within the sample from which imaging information is being obtained;
means for receiving optical reflections from said sample and radiation traveling through said second optical path and responsive at least in part to said received reflections from said sample and received radiation from said second optical path for generating an output having a frequency proportional to the difference in length of the two optical paths corresponding to the longitudinal range in the sample being imaged;
means for detecting said output; and
means for processing the detected output to obtain a selected image of the sample.

200. A system as claimed in claim 199, wherein said second optical path is a loop.

201. A system as claimed in claim 199, wherein said means for controlling the optical characteristic of the radiation source modulates the frequency of output frequency of the source.

202. A system as claimed in claim 199, wherein the frequency modulation is in the form of an FM chirp.

203. A system as claimed in claim 199, wherein said source is linearly chirped.

204. A system as claimed in claim 199, wherein the image of the sample includes gray scale levels to indicate characteristics of the sample.

205. A system as claimed in claim 199, wherein the image of the sample includes a color spectrum to indicate characteristics of the sample.

206. A system as claimed in claim 199, wherein said means for controlling the transverse scanning on the sample includes a movable mirror.

207. A system as claimed in claim 206, wherein the movement of the movable mirror is controlled by a galvanometer.

208. A system as claimed in claim 199, wherein said means for controlling the transverse scanning on the sample includes a pair of movable mirrors to scan the radiation in orthogonal directions.

209. A system as claimed in claim 199, wherein said means for controlling the transverse scanning on the sample includes a rotating polygonal mirror.

210. A system as claimed in claim 199, further including an endoscope for positioning the probe module with respect to the sample.

211. A system as claimed in claim 210, wherein the sample is a tubular structure within the body of a patient.

212. A system as claimed in claim 211, wherein the tubular structure is the esophagus.

213. A system as claimed in claim 211 wherein the tubular structure is the bronchial tree.

214. A system as claimed in claim 211, wherein the tubular structure is the urinary tract.

215. A system as claimed in claim 211, wherein the tubular structure is the genital tract.

216. A system as claimed in claim 199, further including an angioscope for positioning the probe module with respect to the sample.

217. A system as claimed in claim 199, wherein the sample is a blood vessel.

218. A system as claimed in claim 199, further including a second light source for generating a visible beam of radiation to facilitate alignment.

219. A system as claimed in claim 199, wherein each of said first and second optical path includes an optical fiber.

220. A system as claimed in claim 219, wherein at least one end of each optical fiber is angled polished.

221. A system as claimed in claim 219, wherein at least one end of each optical fiber includes an anti-reflection coating.

222. A system as claimed in claim 199, wherein said sample is a biological sample.

223. A system as claimed in claim 222, wherein the biological sample is the eye.

224. A system as claimed in claim 199 further including a memory for storing the results of more than one scan of said sample.

225. A system as claimed in claim 224, wherein said processing means functions to average the results of the scans stored in said memory to improve the image.

226. A system as claimed in claim 199, wherein said image is a non-invasive cross-sectional image of a biological specimen.

227. A system as claimed in claim 199, wherein said means for applying optical radiation from said source through the first and second optical paths includes a first beam splitter for splitting the radiation from the source along said first and second optical paths.

228. A system as claimed in claim 199, wherein said processing means includes an analog to digital converter.

229. A system as claimed in claim 68, further including a polarization controller located in one of the optical paths.

230. A system as claimed in claim 229 wherein said polarization controller functions to match the polarization of the optical radiation in each path.

231. A system as claimed in claim 96 wherein said polarization controller functions to match the polarization of the optical radiation in each path.

232. A system as claimed in claim 121 wherein said polarization controller functions to match the polarization of the optical radiation in each path.

233. A system as claimed in claim 35, further including a polarization controller located in one of the optical paths.

234. A system as claimed in claim 233 wherein said polarization controller functions to match the polarization of the optical radiation in each path.

235. A method as claimed in claim 40 further including the step of controlling the polarization of the radiation in one of the optical paths.

236. A method as claimed in claim 40 further including the step of matching the polarization of the optical radiation in each path.

237. A method as claimed in claim 147 further including the step of controlling the polarization of the radiation in one of the optical paths.

238. A method as claimed in claim 147 further including the step of matching the polarization of the optical radiation in each path.

239. A method as claimed in claim 164 further including the step of matching the polarization of the optical radiation in each path.

240. A system as claimed in claim 169, further including a polarization controller located in one of the optical paths.

241. A system as claimed in claim 240 wherein said polarization controller functions to match the polarization of the optical radiation in each path.

242. A system as claimed in claim 188, further including a polarization controller located in one of the optical paths.

243. A system as claimed in claim 242 wherein said polarization controller functions to match the polarization of the optical radiation in each path.

244. A system as claimed in claim 199, further including a polarization controller located in one of the optical paths.

245. A system as claimed in claim 244 wherein said polarization controller funtions to match the polarization of the optical radiation in each path.

246. A system as claimed in claim 219, further including a polarization controller located in one of the optical paths.

247. A system as claimed in claim 246 wherein said polarization controller functions to match the polarization of the optical radiation in each path.

* * * * *